(12) United States Patent
Ohya et al.

(10) Patent No.: US 8,383,409 B2
(45) Date of Patent: Feb. 26, 2013

(54) CELL CULTURE SUBSTRATE AND ITS PRODUCTION METHOD

(75) Inventors: Shin Ohya, Chuo-ku (JP); Takashi Inoue, Ichihara (JP); Takatoki Yamamoto, Bunkyo-ku (JP); Teruo Fujii, Bunkyo-ku (JP); Yasuyuki Sakai, Bunkyo-ku (JP); Masaki Nishikawa, Bunkyo-ku (JP); Hitomi Sakai, Bunkyo-ku (JP); Hirosuke Naruto, Bunkyo-ku (JP)

(73) Assignees: Kisco Ltd., Osaka-Shi, Osaka (JP); Daisan Kasei Co., Ltd., Tokyo (JP); The University of Tokyo, Tokyo (JP)

( * ) Notice: Subject to any disclaimer, the term of this patent is extended or adjusted under 35 U.S.C. 154(b) by 0 days.

(21) Appl. No.: 13/020,193

(22) Filed: Feb. 3, 2011

(65) Prior Publication Data

US 2011/0136234 A1  Jun. 9, 2011

Related U.S. Application Data

(63) Continuation of application No. 11/889,067, filed on Aug. 8, 2007, now abandoned.

(30) Foreign Application Priority Data

Aug. 8, 2006  (JP) .............................. 2006-215799

(51) Int. Cl.
  *C12N 5/02*  (2006.01)
(52) U.S. Cl. ......... 435/402; 435/395; 435/425; 435/243
(58) Field of Classification Search .................. 435/395, 435/402, 325, 243
  See application file for complete search history.

(56) References Cited

U.S. PATENT DOCUMENTS

| | | | |
|---|---|---|---|
| 2002/0045252 A1* | 4/2002 | Yamashita et al. | 435/325 |
| 2002/0055186 A1* | 5/2002 | Barry et al. | 436/518 |
| 2002/0137222 A1* | 9/2002 | Whitney | 436/86 |
| 2003/0211083 A1* | 11/2003 | Vogel et al. | 424/93.7 |

FOREIGN PATENT DOCUMENTS

| | | | |
|---|---|---|---|
| DE | 4218917 A1 * | 12/1993 | |
| FR | 2663337 A1 * | 12/1991 | |
| GB | 2357288 A | 6/2001 | |
| JP | 2001-233977 A | 8/2001 | |
| JP | 2002-340916 A | 11/2002 | |
| JP | 2006-10565 A | 1/2006 | |
| WO | WO 95/23213 A1 | 8/1995 | |
| WO | WO 97/20569 A2 | 6/1997 | |

OTHER PUBLICATIONS

Machine translation of FR 2663337, Dec. 20, 1991.*
Machine translation of JP 20060010565, Jan. 12, 2006.*
Derwent abstract for DE 4218917; Dec. 16, 1993.*
Martin Chaplin, Water Strucutre and Science, Gelatin downloaded from www.lsbu.ac/water/hygel.htom downloaded Feb. 11, 2012; 2 pages.*
Machine translation of JP 2001-233977A, Aug. 28, 2001.
Machine translation of JP 2002-340916A, Nov. 27, 2002.
Machine translation of JP 2006-010565A, Dec. 2006, provided in U.S. Appl. No. 11/229,067.
US Office Action, dated Nov. 3, 2010, for U.S. Appl. No. 11/889,067.
US Office Action, dated Sep. 23, 2010, for U.S. Appl. No. 11/889,067.

* cited by examiner

*Primary Examiner* — Susan Hanley
(74) *Attorney, Agent, or Firm* — Birch, Stewart, Kolasch & Birch, LLP

(57) ABSTRACT

The invention is directed to methods for the propagation or cultivation of cells including preparing a cell culture substrate, wherein the cell culture substrate includes a substrate and a layer formed by surface modification. The layer includes a polymer containing an amino group. The polymer is produced by reacting a polymer represented by formula (II):

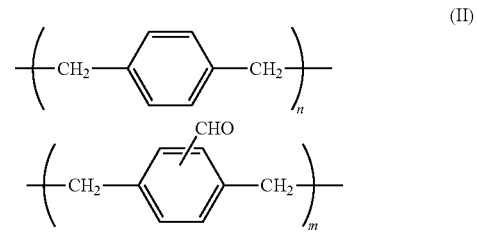

with a polymer having at least one amino group, —$NH_2$, capable of forming a Schiff base in a monomer of formula (II), thereby forming a polymer layer constituting the layer formed by surface modification. "n" in Formula (II) is 0 or a positive integer, and m is a positive integer. n and m represent the degree of polymerization. Formula (II) is formed by chemical vapor deposition of formyl[2.2]paracyclophane. The methods further include providing cells in a medium; inoculating the cells onto the cell culture substrate; and culturing the cells, wherein the cells adhere to the cell culture substrate.

13 Claims, 43 Drawing Sheets

CELL CULTURE SUBSTRATE AND ITS PRODUCTION METHOD

This application is a Continuation of application Ser. No. 11/889,067, filed on Aug. 8, 2007, now abandoned, which claims the benefit of priority of Japanese Patent Application No. 2006-215799, filed Aug. 8, 2006. The entire contents of each are hereby incorporated be reference.

TECHNICAL FIELD

This invention relates to a cell culture substrate, and more specifically, to a substrate adapted for use in the propagation and cultivation of the cells used in the field of biology, medicine, immunology, and the like. Still more specifically, this invention relates to a cell culture substrate adapted for use in cultivating embryonic stem cells (ES cells) of an animal such as mouse, monkey, and ape and functional tissue cells used in artificial skin, artificial bone, artificial organ, and the like; and a method for providing a layer formed by surface modification on the surface of the cell culture substrate.

BACKGROUND ART

Animal and plant cells have been cultivated by various cultivation techniques. The technique of cell cultivation is one of the basic techniques used in various biological fields. In the fields of life sciences, this technique of cell cultivation is particularly indispensable in developing drugs and elucidating the pathological mechanism. In recent years, cultivation techniques have been developed not only for research purpose but also for use in commercial scale cultivation of the cells in the biology, medicine, immunology, and other fields. For example, in the field of medicine, tissue cells are cultivated for use in prosthetics such as artificial organ, artificial mandible, and artificial skin.

In such cell cultivation, the cells are cultivated in a certain container with a culture medium containing nutrient components. The cell cultures are divided by its nature into two major categories, namely, the cell culture floating in the culture medium and the cell culture attached to the bottom surface of the container. Many animal cells are anchorage dependent, and they only grow when the they are attached to a substrate, and they are incapable of surviving for a long time when they are flowing in the culture medium. Accordingly, a substrate for adhesion of the cells is required in cultivating such anchorage dependent cells.

Examples of typical cell culture substrate used in laboratories include dish, flask, and multi plate, and commercially available such substrates include those prepared by providing a surface of a polystyrene molded article with hydrophilicity by low temperature plasma treatment, corona discharge treatment, and the like. These devices are widely used in the cultivation of anchorage dependent cells including fibroblast, smooth muscle cell, endothelial cell, and cornea cell for both established cells and initial cells. These devices are also widely used for non-anchorage dependent floating cells such as lymphocytes which have been established as a blood cell line.

However, some cells exhibit insufficient growth or unfavorable growth morphology even if such cell propagated on these cell culture devices, and this situation is significant in the case of initial culture. In view of such situation, the cultivation surface of the container has often been coated with an extracellular matrix such as collagen, gelatin or a adhesion factor such as fibronectin, laminin, and vitronectin to thereby improve adhesion and propagation ability of the cells.

For example, non-patent documents 1, 2, 3, and 4 and patent documents 1, 2, and 3 as described below disclose production of cultivated epithelium and epidermis by using a dish coated with collagen, a collagen gel, a collagen sponge, a collagen sheet having a three dimensional structure produced by molecular crosslinking, a collagen sponge formed with through holes, and the like for the cell culture substrate, inoculating a cell such as human fibroblast or human keratinocyte on such substrate, and cultivating the cell; and producing cultivated mucosa and skin by forming a layer of human keratinocyte on the human fibroblast.

The collagen used in forming the collagen coating layer is Type I collagen from connective tissue of an animal which has been solubilized by using an acid or enzyme. The collagen coated layer can be produced by coating this collagen on a culture dish or the like followed by drying. A typical example of the collagen which can serve such cell culture substrate is the one solubilized and extracted from bovine or porcine connective tissue. However, use of such bovine or porcine collagen has become increasingly difficult in view of the problems such as BSE (bovine spongiform encephalopathy) and foot and mouth disease. In addition, there is a need for a cell cultivation method which has an improved cell propagation efficiency than the method using such conventional cell culture substrate.

In cultivating a neural cell, a surface having coated thereon a polylysine such as poly-D-lysine and poly-L-lysine is often used. The polylysine coating facilitates adhesion of the neural cell, and neural cell lines cultivated by using such coating exhibit good propagation morphology with sufficient extension of the neurite.

As described above, the polylysine has various favorable properties for the cultivation of neural cells. The polylysine, however, has a drawback of insufficient stability. When a polylysine is coated on the cultivation device commonly used in the art as described above, the activity of polylysine is lost in 2 weeks when stored at room temperature, and in 1 month when stored at 4° C. In addition, the coated device can not be sterilized because of such insufficient stability. Accordingly, use of a cultivation device coated with the polylysine requires an inconvenient step of coating of the polylysine in a sterile environment on a preliminarily sterilized cultivation device before its use, and this is a quite complicated process, and the thus prepared device could be stored only for about 1 month even if stored in the refrigerator.

As described above, coating of the polylysine on the cultivation device commonly used in the art takes considerable amount of work, and one reason has been the instability of the polylysine after its coating. In addition, this coating required use of a sterile environment such as use of a clean bench. Accordingly, selling of a cell cultivation device having the polylysine preliminarily coated thereon would need a number of steps carried out in sterile environment as well as storage under controlled environment that would result increase in the cost.

Non-Patent Document 1: Rinsho Kagaku (The Journal of Clinical Science), vol. 34, No. 9, Y. Shirakata and K. Hashimoto, "Regenerative medicine X: regeneration mechanism of skin-epidermis and burn treatment using cultivated epidermis sheet", pages 1283 to 1290

Non-Patent Document 2: Nagoya University Press, issued on 1999/10/10, "Fundamentals and application of textile engineering: Tissue engineering" ed. by M. Ueda, K. Matsuzaki and N. Kumagaya, Cultured skin, pages 107 to 117

Non-Patent Document 3: M. Ueda and K. Hata, Skin and Mucosa, Pharma Media Vol. 18, No. 1, 2000, pages 25 to 29, 2000

Non-Patent Document 4: Nagoya University Press, issued on 1999/10/10, "Basic and applied textile engineering: Tissue engineering" ed. by M. Ueda, M. Ueda and K. Hata, oral mucosa, pages 118 to 127

Patent Document 1: Japanese Patent Application Laid-Open No. 6-292568
Patent Document 2: Japanese Patent Application Laid-Open No. 8-243156
Patent Document 3: Japanese Patent Application Laid-Open No. 9-47503

SUMMARY OF THE INVENTION

An object of the present invention is to provide a cell culture substrate which is durable and which can be readily produced in commercial scale at a low cost. Another object of the present invention is to provide a production method of such cell culture substrate.

The inventors of the present invention proposed a DNA chip coated with poly-p-xylylene having amino group added thereto in Japanese Patent Application Laid-Open No. 2004-189740. After this patent application, the inventors found that biocompatibility of various material can be improved by coating the material with the layer of poly-p-xylylene having amino group added thereto. Although the coating of a poly-p-xylylene layer has been used in a stent, a pace maker, and the like, this layer of poly-p-xylylene used itself is highly hydrophobic, and this layer has little if any cell adhesion or cell adsorption property required for a substrate used in the cell cultivation.

However, addition of amino group to the poly-p-xylylene layer can improve such high hydrophilicity and absence of the cell adhesion or adsorption property.

Accordingly, the objects of the invention are realized by providing the present invention constituted as described below.

(1) A cell culture substrate comprising a substrate and a layer formed by surface modification, said layer comprising a polymer containing amino group produced by reacting a polymer represented by the following formula (II):

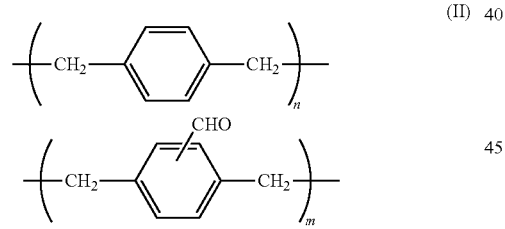

(wherein n is 0 or a positive integer, and m is a positive integer, the n and m representing degree of polymerization) formed by chemical vapor deposition of formyl[2.2]paracyclophane represented by the following formula (I):

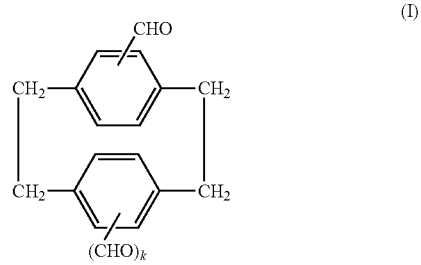

(wherein k is 0 or 1) with a polymer having at least one amino group (—NH$_2$) capable of forming Schiff base in its monomer.

(2) The cell culture substrate according to the above (1) wherein the polymer containing amino group constituting the layer formed by surface modification is represented by the following formula (III):

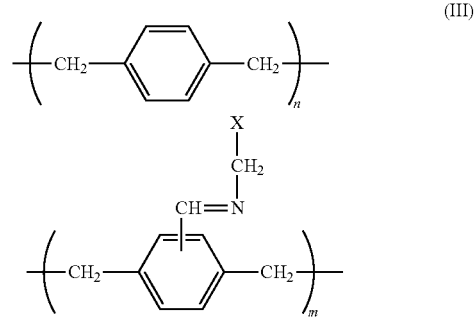

(wherein n is 0 or a positive integer, m is a positive integer, X represents a group having primary amine wherein amino group is bonded directly to the carbon atom in the polymer backbone or via an intervening alkylene group containing 1 to 4 carbon atoms to carbon or nitrogen in the polymer backbone).

(3) The cell culture substrate according to claim 1 wherein the polymer having amino group constituting the surface modified layer is represented by the following formula (IV):

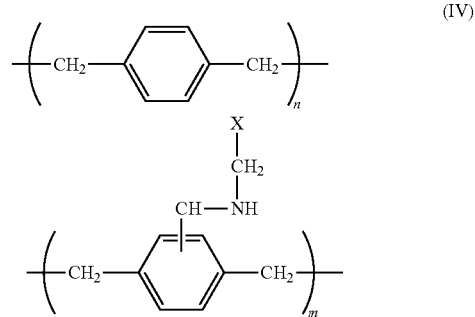

(wherein n is 0 or a positive integer, m is a positive integer, X represents a group having primary amine wherein amino group is bonded directly to the carbon atom in the polymer backbone or via an intervening alkylene group containing 1 to 4 carbon atoms to carbon or nitrogen in the polymer backbone).

(4) The cell culture substrate according to the above (2) or (3) wherein the polymer backbone in X in the formula (III) or (IV) is polyethylene, polyethyleneimine, or polymethylene amide.

(5) The cell culture substrate according to any one of the above (2) to (4) wherein, in the formula (III) or (IV), X is bonded to —CH$_2$ via carbon or nitrogen.

(6) The cell culture substrate according to any one of the above (1) to (5) wherein the polymer represented by the formula (II) is formed by chemical vapor deposition of formyl [2.2]paracyclophane represented by the formula (I) on the underlying layer of chloro-substituted [2.2]paracyclophane.

(7) The cell culture substrate according to any one of claims 1) to (6) wherein the substrate is a three dimensional structure.

(8) A method for producing a cell culture substrate comprising a substrate and a layer formed by surface modification, comprising the steps of
forming a layer of a polymer represented by formula (II):

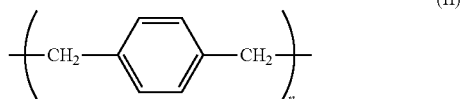
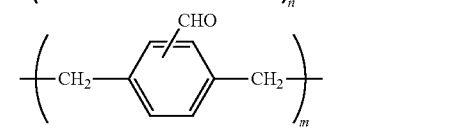

(II)

(wherein n is 0 or a positive integer, and m is a positive integer, the n and m representing degree of polymerization) on the substrate by conducting chemical vapor deposition of formyl [2.2]paracyclophane represented by the following formula (I):

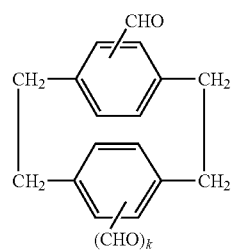

(I)

(wherein k is 0 or 1); and
reacting the layer of the polymer represented by the formula (II) with a polymer having at least one amino group (—NH$_2$) capable of forming Schiff base in its monomer to obtain a layer of a polymer represented by the formula (III):

$$\left(\!-\mathrm{CH_2}\!-\!\!\bigcirc\!\!-\mathrm{CH_2}\!-\!\right)_{\!n}$$
$$\overset{\underset{\mathrm{CH_2}}{\mathrm{X}}}{\underset{\mathrm{CH}=\mathrm{N}}{|}}$$
$$\left(\!-\mathrm{CH_2}\!-\!\!\bigcirc\!\!-\mathrm{CH_2}\!-\!\right)_{\!m}$$

(III)

(wherein n is 0 or a positive integer, m is a positive integer, X represents a group having primary amine wherein amino group is bonded directly to the carbon atom in the polymer backbone or via an intervening alkylene group containing 1 to 4 carbon atoms to carbon or nitrogen in the polymer backbone), this polymer layer constituting the layer formed by surface modification.

(9) The method for producing a cell culture substrate according to the above (8) wherein said reaction is conducted by immersing the polymer in a solution containing the polymer containing amino group (—NH$_2$).

(10) The method for producing a cell culture substrate according to the above (9) wherein the solution containing the polymer containing amino group (—NH$_2$) has the polymer concentration of 0.1 to 0.00001%.

(11) The method for producing a cell culture substrate according to anyone of the above (8) to (10) further comprising the step of
reducing the polymer represented by the formula (III) to obtain the layer of a polymer represented by the formula (IV)

$$\left(\!-\mathrm{CH_2}\!-\!\!\bigcirc\!\!-\mathrm{CH_2}\!-\!\right)_{\!n}$$
$$\overset{\underset{\mathrm{CH_2}}{\mathrm{X}}}{\underset{\mathrm{CH}-\mathrm{NH}}{|}}$$
$$\left(\!-\mathrm{CH_2}\!-\!\!\bigcirc\!\!-\mathrm{CH_2}\!-\!\right)_{\!m}$$

(IV)

(wherein n is 0 or a positive integer, m is a positive integer, X represents a group having primary amine wherein amino group is bonded directly to the carbon atom in the polymer backbone or bonded via an intervening alkylene group containing 1 to 4 carbon atoms to carbon or nitrogen in the polymer backbone), this polymer layer constituting the layer formed by surface modification.

BEST EMBODIMENT FOR CARRYING OUT THE INVENTION

Figure 1:
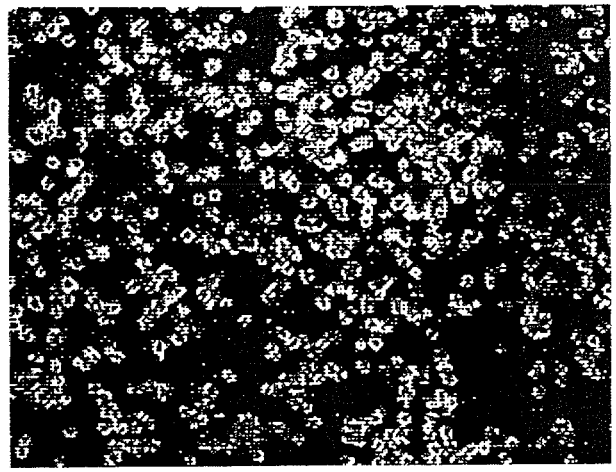
FIG. 1 shows conditions of the culture of Example 1, Sample No. 1 after 6 hours.
Figure 2:
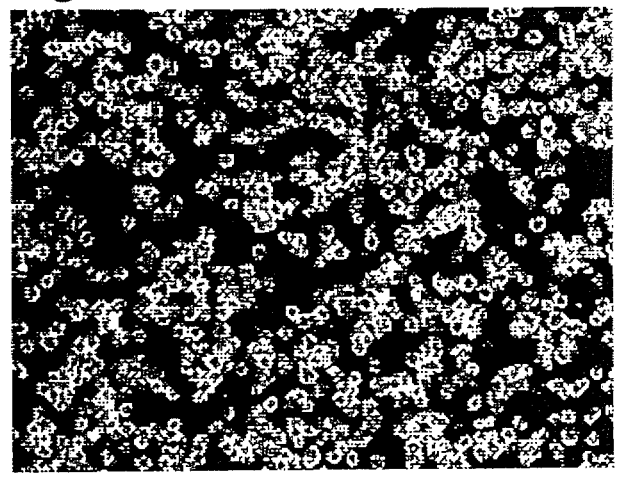
FIG. 2 shows conditions of the culture of Example 1, Sample No. 2 after 6 hours.
Figure 3:
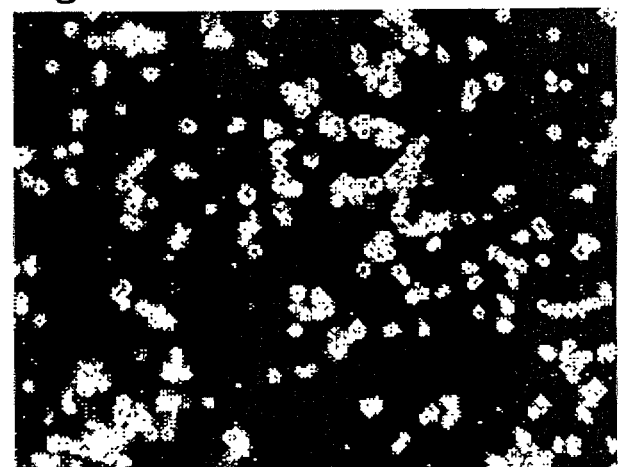
FIG. 3 shows conditions of the culture of Example 1, Sample No. 3 after 6 hours.
Figure 4:
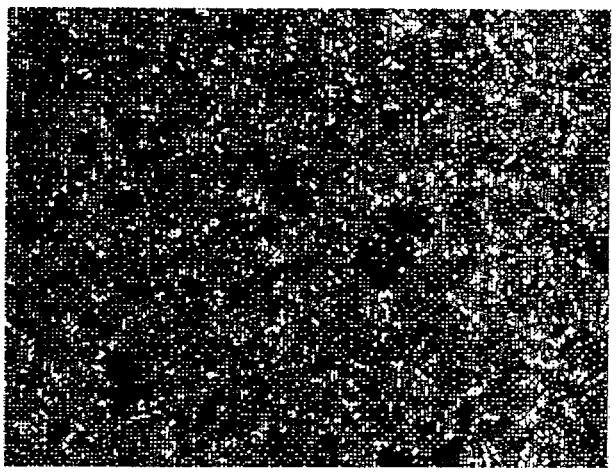
FIG. 4 shows conditions of the culture of Example 1, Sample No. 4 after 6 hours.
Figure 5:
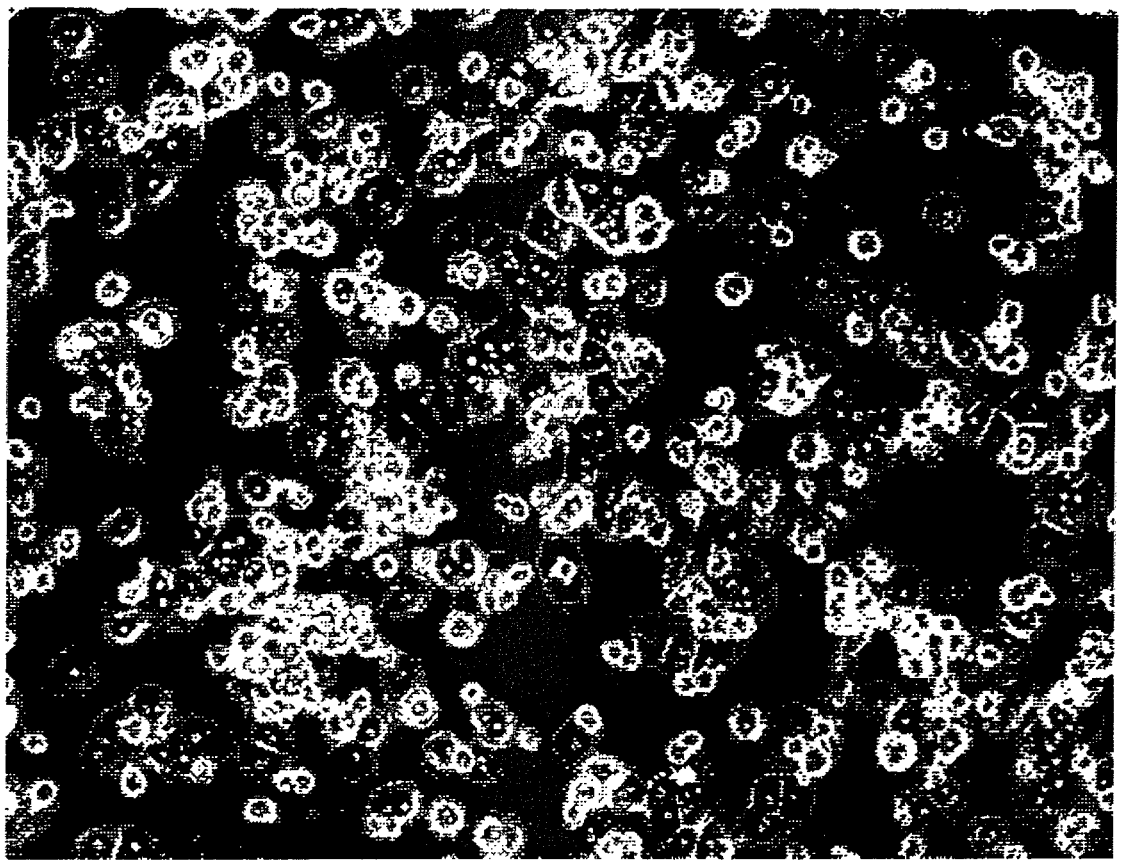
FIG. 5 shows conditions of the culture of Example 1, Sample No. 5 after 6 hours.
Figure 6:
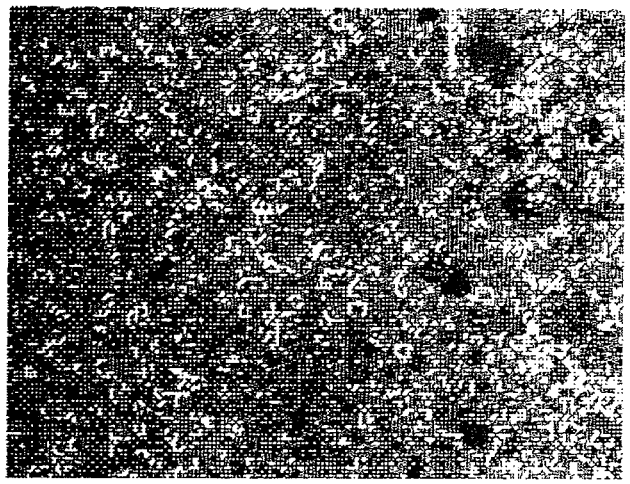
FIG. 6 shows conditions of the culture of Example 1, Sample No. 1 after 2 days.
Figure 7:
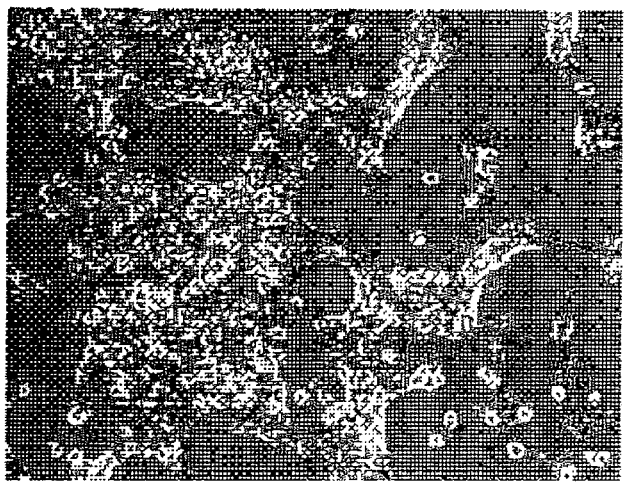
FIG. 7 shows conditions of the culture of Example 1, Sample No. 2 after 2 days.
Figure 8:
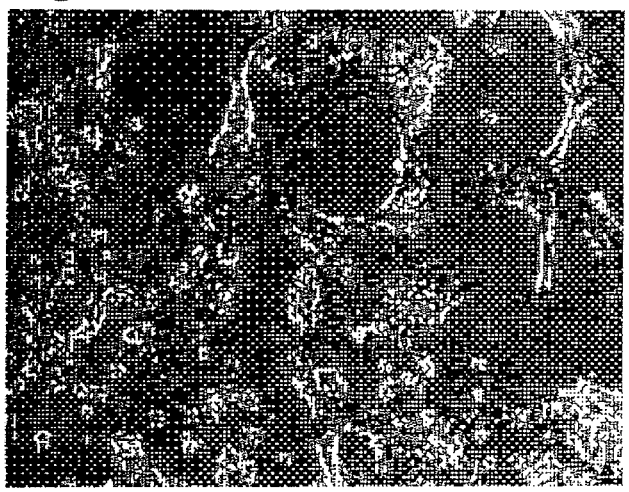
FIG. 8 shows conditions of the culture of Example 1, Sample No. 3 after 2 days.
Figure 9:
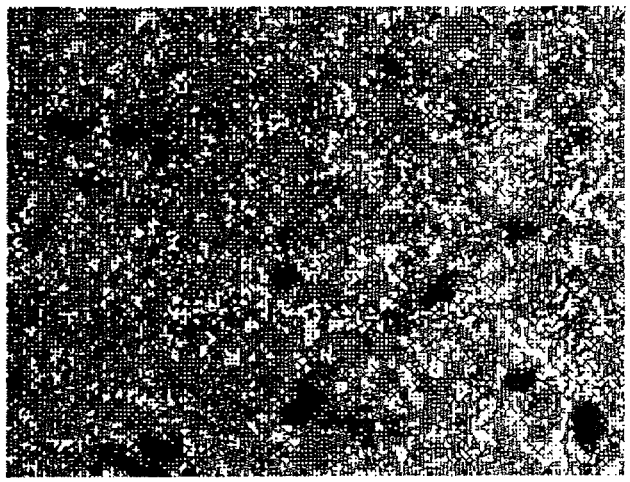
FIG. 9 shows conditions of the culture of Example 1, Sample No. 4 after 2 days.
Figure 10:
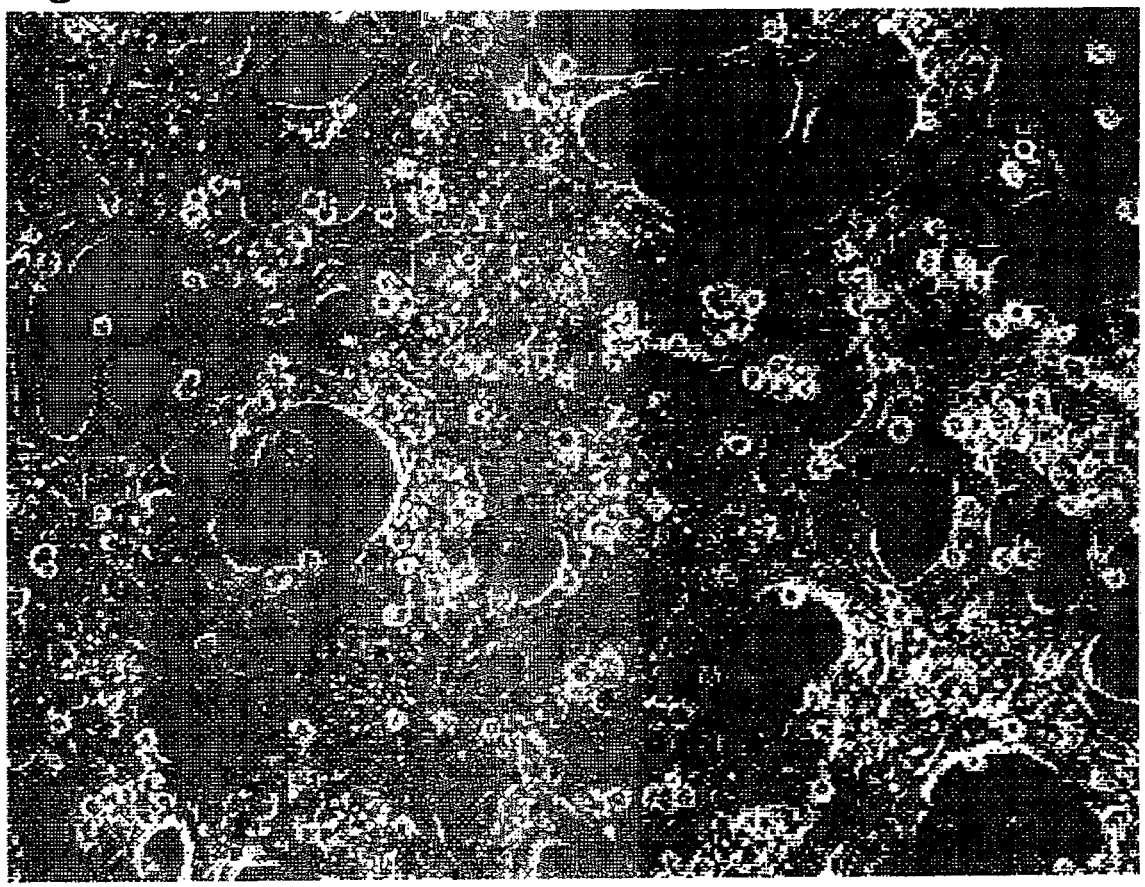
FIG. 10 shows conditions of the culture of Example 1, Sample No. 5 after 2 days.
Figure 11:
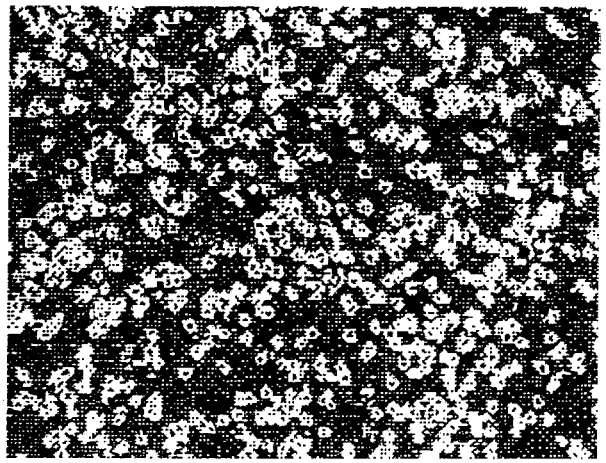
FIG. 11 shows conditions of the culture of Example 1, Sample No. 1 after 4 days.
Figure 12:
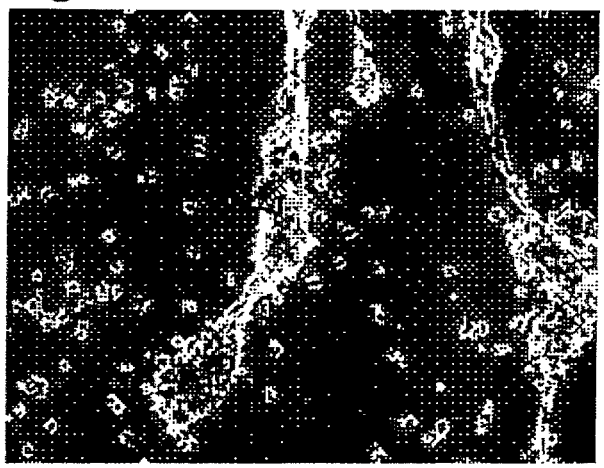
FIG. 12 shows conditions of the culture of Example 1, Sample No. 2 after 4 days.
Figure 13:
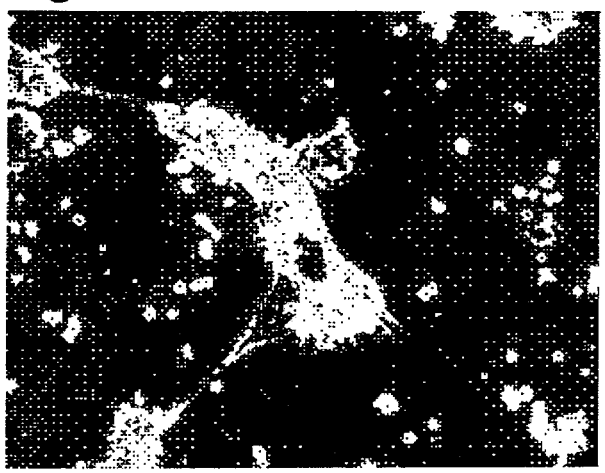
FIG. 13 shows conditions of the culture of Example 1, Sample No. 3 after 4 days.
Figure 14:
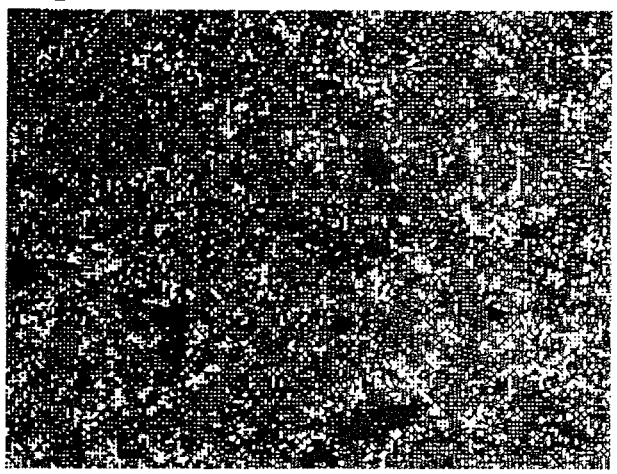
FIG. 14 shows conditions of the culture of Example 1, Sample No. 4 after 4 days.
Figure 15:
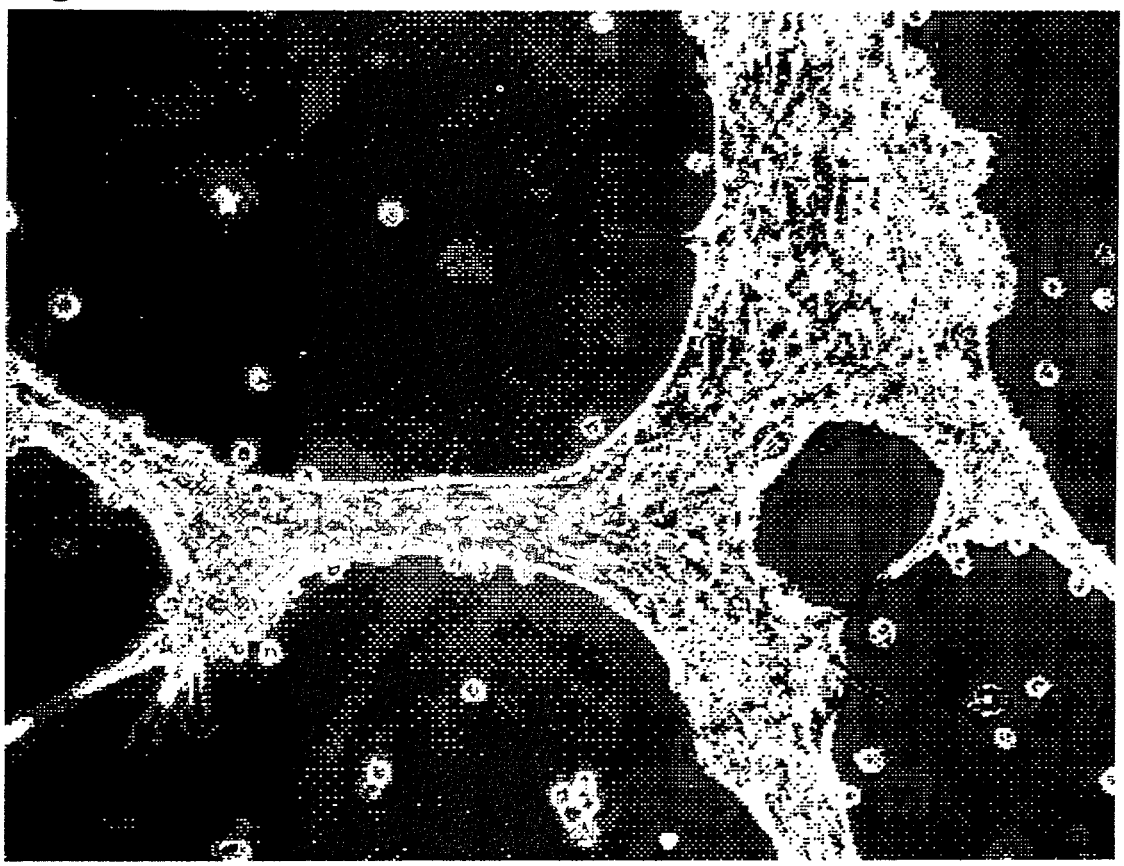
FIG. 15 shows conditions of the culture of Example 1, Sample No. 5 after 4 days.

The cell culture substrate of the present invention comprises a substrate and a layer formed by surface modification. The layer formed by surface modification comprises a polymer containing amino group produced by reacting a polymer represented by the following formula (II):

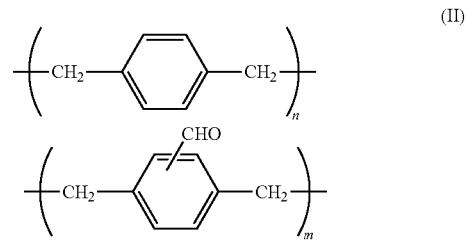

(wherein n is 0 or a positive integer, and m is a positive integer, the n and m representing degree of polymerization) formed by chemical vapor deposition of formyl[2.2]paracyclophane represented by the following formula (I):

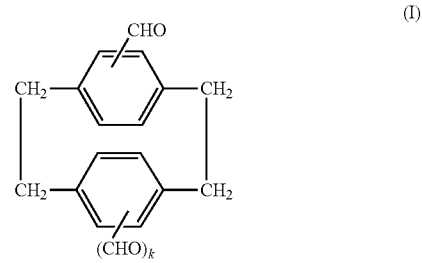

(wherein k is 0 or 1) with a polymer having at least one amino group (—$NH_2$) (an amino group-containing polymer) capable of forming Schiff base in its monomer.

The thus produced polymer has the merit that hydrophilicity, affinity for the cell, and adhesion to the cell can be dramatically improved, since the number of amino group introduced in the polymer can be increased by selecting the amino group-containing polymer used for the reaction.

The amino-containing polymer used in the present invention is not particularly limited as long as its monomer unit contains at least one amino group (—$NH_2$) that undergoes condensation and dehydration by reacting with the formyl group of the formyl[2.2]paracyclophane to generate the compound represented by the general formula RR'C═NR" or (—CH═N—), namely, the Schiff base in the monomer unit. The amino group that was not used in the formation of the Schiff base contributes for the improvement of the hydrophilicity, affinity for various cells, and adhesion to various cells. Accordingly, inclusion of a higher number of amino groups is preferable in view of improving the hydrophilicity, affinity for the cell, and adhesion to the cell. However, an excessive number of the amino groups may adversely affect such merits. The amino group which is not involved in the generation of the Schiff base is preferably —NH$_2$. Such amino group, however, may also be —NHR or —N(R)$_2$ wherein R represents a substituent such as alkyl group. Exemplary such polymers include those derived from a primary amine compound having a polymerizable unsaturated group (ethylenically unsaturated group) such as vinyl group. Such polymer may preferably have a molecular weight (weight average molecular weight) of 1,000 to 500,000.

Examples of such amino-containing polymer include those as described below.

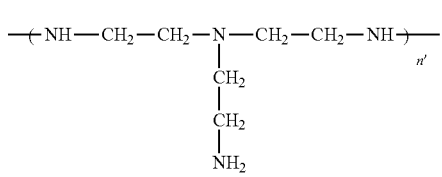
(1)

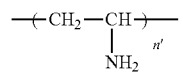
(2)

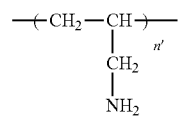
(3)

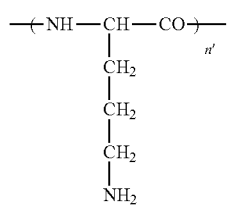
(4)

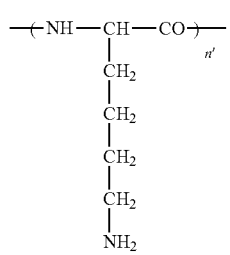
(5)

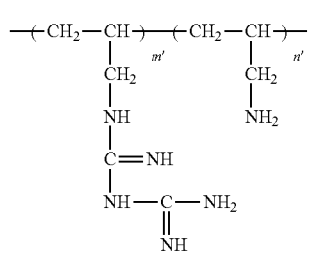
(PAB)

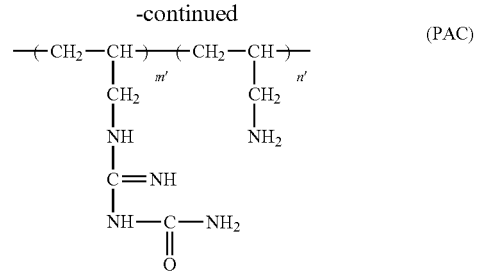
(PAC)

wherein m' and n' respectively represent degree of polymerization.

These polymers include commercially available polymers which may be used with no further treatment. The polymer may also be synthesized by repeating or modifying the method known in the art.

Among these, the most typically used are the compounds of (1) to (5). For example, the polyethyleneimine compound of (1) is commercially available under the product name of EPOMIN (manufactured by Nippon Shokubai), and the polyallylamine compound of (3) is commercially available under the product names of PAA-L (weight average molecular weight, 10,000) and PAA-H (weight average molecular weight, 100,000) (both manufactured by Nittobo).

These polymers are typically used alone. However, if desired, they may be used in combination of two or more.

Preferable examples of the polymer containing the amino group produced by reacting the chemically deposited formyl [2.2]paracyclophane represented by the formula (I) with the alkyl-containing polymer include the Schiff base polymer represented by the formula (III) and the polymer represented by the formula (IV) which is produced by reducing the Schiff base moiety of such Schiff base polymer.

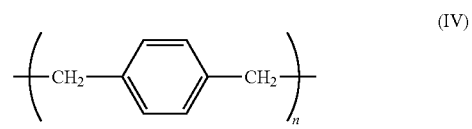
(IV)

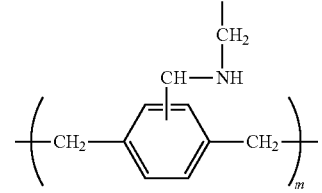

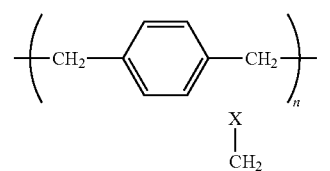
(III)

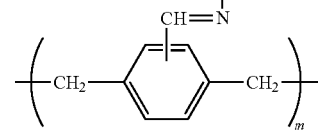

In the formulae (III) and (IV), n and m respectively represent degree of polymerization, and n is an integer of at least 0, and m is an integer of at least 1 with the proviso that n+m is at least 2; and X represents a group having primary amine wherein amino group is bonded directly to the carbon atom in the polymer backbone or via an intervening alkylene group containing 1 to 4 carbon atoms to carbon or nitrogen in the polymer backbone).

The polymer backbone of X is preferably polyethylene, polyethyleneimine, or polyethylene amide as in shown above the exemplary compounds of the amino-containing polymer. X is typically bonded to the —$CH_2$ at carbon or nitrogen.

The polymer represented by the formula (II) is postulated to be typically a random copolymer.

The layer formed by surface modification containing such polymer containing the amino group is not limited for its thickness, and an adequate thickness may be selected depending on the intended application of the product.

In forming the layer formed by surface modification of the present invention, an underlying layer is preferably formed by chemically depositing a chloro-substituted [2.2]paracyclophane, and preferably dichloro [2.2]paracyclophane before chemically depositing the formyl[2.2]paracyclophane represented by the formula (I).

The layer of a polychloro-substituted [2.2]p-xylylene exhibits stronger adhesion to the substrate, and the adhesion of the substrate and the surface modification layer is improved by the provision of such layer. As a consequence, handling convenience as well as durability are improved, and for example, peeling of the layer during the handling of the substrate is prevented. As mentioned above, such improvement is also economically advantageous.

The thickness of the underlying layer is not particularly limited as long as the improvement in the adhesion is realized, and an adequate thickness may be selected depending on the thickness of the surface modification layer. The underlying layer is typically formed to a thickness thicker than the surface modification layer.

In forming the surface modification layer of the present invention, the formyl[2.2paracyclophane represented by the formula (I) is first synthesized.

The formyl[2.2]paracyclophane represented by the formula (I) is obtained by reacting [2.2]paracyclophane with dichloromethylmethyl ether in the presence of titanium chloride (IV).

Next, a polymer layer is formed on the substrate by using the thus produced formyl[2.2]paracyclophane represented by the formula (I) as the source.

The compound represented by the formula (I) can be produced into a consistent layer stably adhered to the underlying substrate when this source material is evaporated and decomposed and subsequently polymerized and deposited on the substrate preferably by vapor deposition, and in particular, by CVD. More specifically, this process may be conducted by evaporating the source material at a predetermined temperature to form a dimer gas, heating this dimer gas to its decomposition temperature to form a monomer gas, and polymerizing and depositing this monomer gas onto the substrate under the predetermined degree of vacuum.

Figure 52:
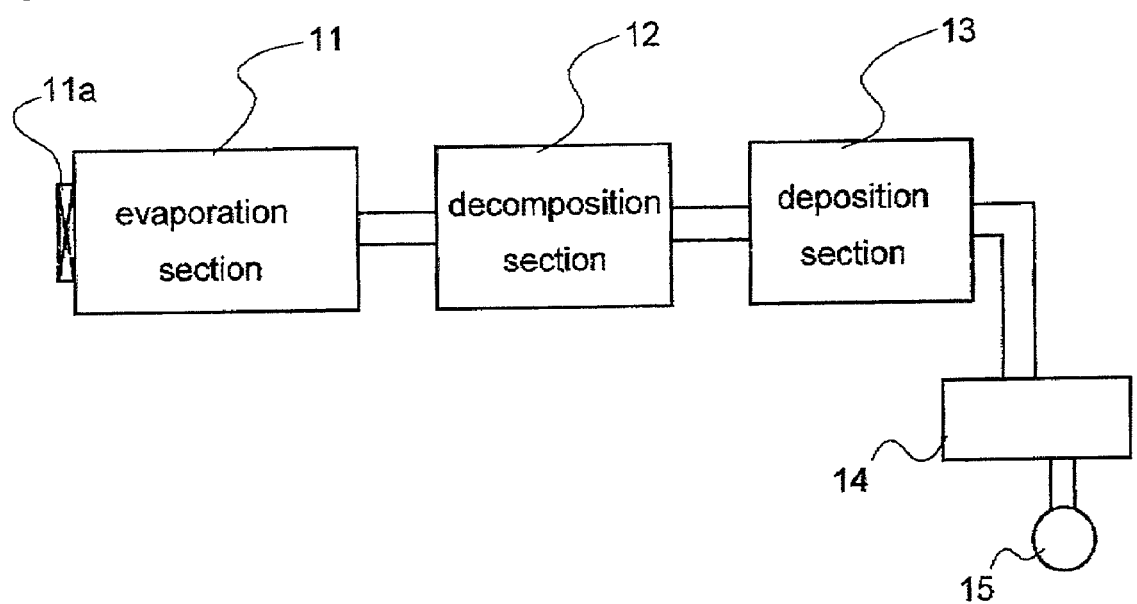
FIG. 52 is a block diagram showing schematic constitution of the apparatus used for producing the polymer layer of the present invention.

The chemical vapor deposition may be accomplished, for example, by the vapor deposition apparatus as shown in FIG. 52. This vapor deposition apparatus has a evaporation section 11, a decomposition section 12, and a deposition section 13. As shown in FIG. 52, the evaporation section 11 is provided with a shutter 11a at the opening for introducing the evaporation source, and the evaporation section 13 is connected to a vacuum pump 15 by an intervening trap 14.

In the vapor deposition apparatus shown in FIG. 52, the evaporation source, namely, the formyl[2.2]paracyclophane represented by the formula (I) in solid state is introduced in the evaporation section 11. When the evaporation section 11 is placed in the vacuum at a degree of about 10 to 75 mTorr (1.33 to 10.0 Pa) and heated to about 100 to 180° C., a dimer gas is produced by vaporization of the evaporation source, and the source gas is thereby produced.

Next, the thus produced dimer gas of the evaporation source is heated to about 700° C., and introduced in the decomposition section 12. In this decomposition section 12, the introduced source gas is converted into a monomer gas by thermal decomposition.

Next, the source monomer gas produced is introduced in the deposition section 13 which is maintained at a degree of vacuum of about 75 mTorr (10.0 Pa) at the maximum. The introduce monomer gas polymerizes on the surface of the substrate, and the layer of the polymer represented by the formula (II) is thereby formed.

This process of layer deposition is preferably conducted in a non-oxidizing atmosphere containing the oxygen at an extremely low content (for example, nitrogen atmosphere) in order to prevent oxidation of the formyl group. In particular, the deposition chamber should be filled with a non-oxidizing atmosphere (for example, nitrogen atmosphere) as soon as possible, and the subsequent process is also preferably conducted in a non-oxidizing atmosphere (for example, nitrogen atmosphere).

Before forming the layer of formyl[2.2]paracyclophane represented by the formula (I) by the chemical vapor deposition, chloro-substituted [2.2]paracyclophane may be deposited on the substrate by chemical vapor deposition to thereby form a layer of the polymer of the chloro-substituted [2.2]paracyclophane. In this case, the layer of the polymerized formyl[2.2]paracyclophane represented by the formula (I) is formed on the layer of the polymerized chloro-substituted [2.2]paracyclophane. This improves adhesion of the layer of the polymerized formyl[2.2]paracyclophane with the substrate, and peeling of the layer by mechanical stress will be prevented. Provision of such underlying layer is also economically advantageous as described above. For further improvement of the adhesion, a coupling agent may be placed between the layer of the polymerized formyl[2.2]paracyclophane and the substrate.

Next, the poly(formyl-p-xylylene) represented by the formula (II) formed on the substrate is reacted with an amino group-containing polymer to obtain the polymer represented by the formula (III) wherein a Schiff base has been formed by the condensation reaction between the formyl group and the amino group.

The reaction of the poly(formyl-p-xylylene) and the amino group-containing polymer may be accomplished, for example, by dissolving the amino-containing polymer in a solvent such as alcohol, and immersing the substrate having the poly(formyl-p-xylylene) layer formed thereon in this solution, for example, at room temperature for about 30 minutes to 4 hours, and preferably for about 1 to 3 hours. Although the reaction may be facilitated by shaking the container or stirring the solvent, care should be taken for prevention of the bubble formation. Concentration of this solution may differ by the type of the amino group-containing polymer and the solvent used. In the case of the solution prepared by dissolving the polyallylamine in an alcohol (preferably ethanol), the solution may typically have a concentration of up to 0.1% with the lower limit of about 0.00001%, and preferably 0.0001%, and more preferably, the solution may have a concentration in the range of 0.01 to 0.001% since intended benefits are less likely to be realized by the polyallylamine used at a concentration outside such range.

Presence of the Schiff base can be confirmed, for example, by analysis using FT-IR.

In the present invention, the surface modification layer may comprise the polymer represented by the formula (III), and such layer is sufficient. However, the Schiff base moiety of this compound may be further reduced by using a reducing agent such as $NaBH_4$ to thereby obtain the polymer represented by the formula (IV) and produce the surface modification layer comprising such polymer represented by the formula (IV). Although the polymer represented by the formula (IV) is superior in the stability, the surface modification layer of the present invention may either comprise the compound represented by formula (III) or (IV) or a combination of both polymers.

The formation of the Schiff base polymer may be confirmed by observing the hydrophilicity, affinity for the cell, and adhesion to the cell.

The surface modification layer containing the polymer represented by the formula (III) or (IV) is thereby produced.

In the present invention, the surface modification layer may be formed by mask vapor deposition using a mask of a predetermined pattern to thereby enable formation of the surface modification layer of a particular pattern at an increased accuracy, or to prevent formation of the surface modification layer at certain part of the substrate. Use of such mask in the vapor deposition may prevent formation of the cell membrane or tissue in the unnecessary part of the substrate, and enable, for example, formation of a particular neuron circuit or a particular organ on the substrate.

The reaction scheme as described above may be summarized as shown below, wherein the reactions are shown for the case wherein k is 0 in the formula (I).

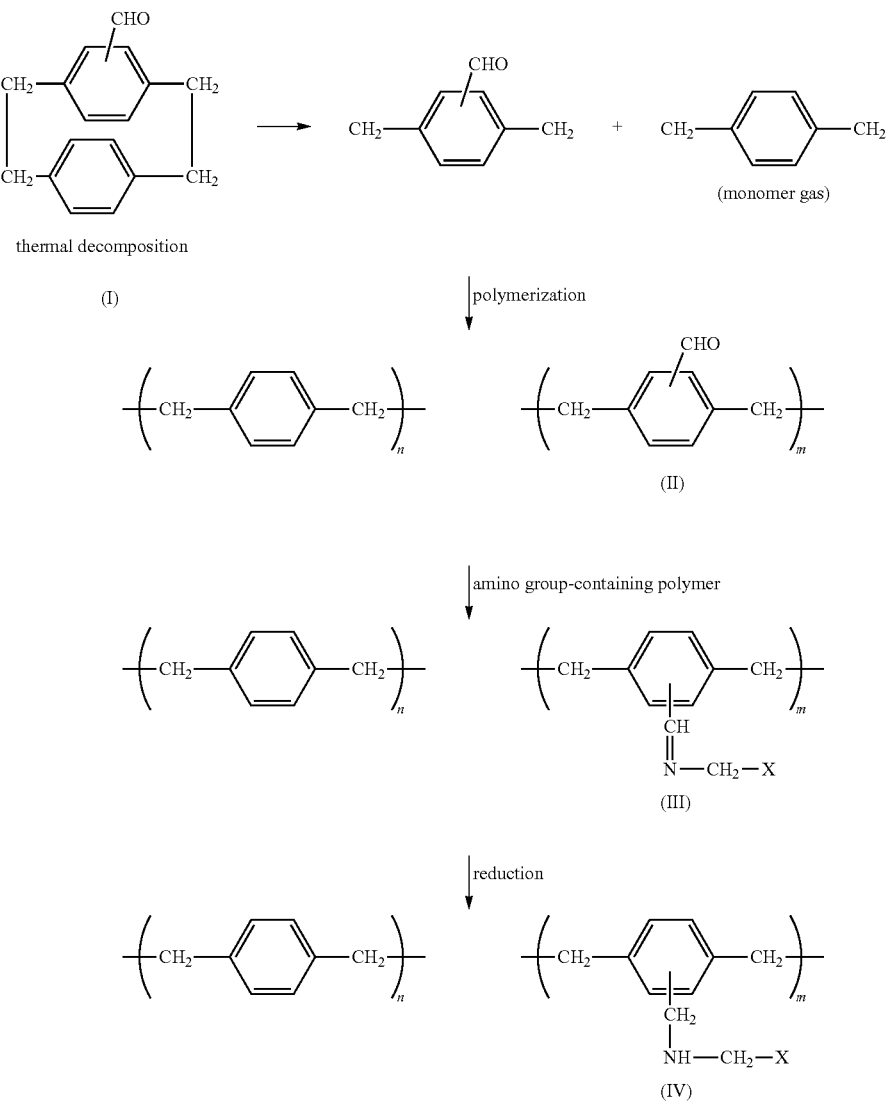

In this reaction scheme, n, m, and X are as defined above for the formulae (III) and (IV).

The cell culture substrate of the present invention is provided by forming the surface modification layer as described above on a substrate. The substrate may comprise a transparent glass or a polymer such as silicone, polyethylene terephthalate, cellulose acetate, bisphenol A carbonate or other carbonate, polystyrene, or polymethyl methacrylate. Other materials such as paper, metal, and fiber may also be used for the substrate. When the cell culture substrate is used by inserting in a living body or in constituting three dimensional structure, the substrate used preferably comprises a material which has properties such as tissue compatibility and biodegradability.

EXAMPLES

Example 1

Synthesis of Starting Materials

The formyl[2.2]paracyclophane represented by the formula (I) was synthesized from [2.2]paracyclophane by the procedure as described below.

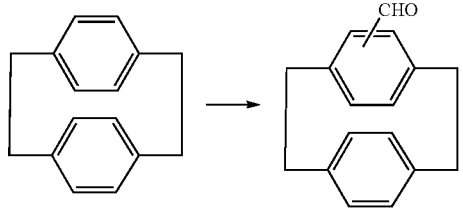

7.8 g of [2.2]paracyclophane was suspended in 40 ml of methylene chloride. 80 ml of solution of titanium chloride (IV) in methylene chloride (concentration, 1 mol/L) was added to this suspension, and the mixture was cooled to a temperature in the range of 0° C. to 5° C. 9.0 g of solution of dichloromethylmethyl in ether was added dropwise at this temperature with stirring. After completing the dropwise addition, the mixture was stirred for another 20 minutes at room temperature. The mixture was then poured onto an ice containing 50 ml of hydrochloric acid. Methylene chloride solution was separated, and this solution was washed twice with 200 ml of water. The methylene chloride solution was dehydrated with sodium sulfate in nitrogen atmosphere, and the solvent was removed by distillation in nitrogen atmosphere. 200 ml of ethanol was added to the residue, and the mixture was refluxed with heating. The turbid solution was filtered. The ethanol solution was condensed and allowed to cool. The resulting precipitate was collected by filtration, and dried under reduced pressure to obtain 5.2 g of formyl[2.2]paracyclophane (purity determined by gas chromatography (GC), 99.8%; mp, 140 to 142° C.)

[Treatment of the Underlying Layer]

Before forming the polymer layer, a layer with the thickness of 3 μm was formed as an underlying layer on the polystyrene dish (diameter, 90 mm; height, 15 mm) used for the substrate by chemical vapor deposition of the dichloro[2.2]paracyclophane. The formation of this underlying layer was conducted by vapor deposition apparatus as shown in FIG. 1. In the vapor deposition, 8.4 g of dichloro [2,2]paracyclophane (a solid vapor deposition source) was placed in the evaporation section of the vapor deposition apparatus as shown in FIG. 52, and the evaporation section was gradually heated to a temperature of 140 to 180° C. while maintaining the evaporation section at a vacuum of 10 to 30 mTorr (1.33 to 4.0 Pa) for vaporization into a dimer gas to thereby provide the source gas. The thus generated source gas was introduced in a decomposition section that had been heated to 600° C. In this decomposition section, the source gas introduced was thermally decomposed into a monomer gas, and the thus produced monomer gas was introduced in the evaporation section kept at a vacuum of 30 mTorr (4.0 Pa) at the maximum. The monomer gas introduced was polymerized on the surface of the polystyrene substrate placed in the evaporation section to thereby form the underlying layer. The underlying layer formed had a thickness of 3 μm.

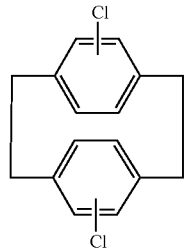

[Production the Substrate Having the Layer Formed by Surface Modification]

(1) Formation of the Polymer Layer

Next, 10.0 g of formyl[2.2]paracyclophane (solid evaporation material) having the structure represented by the formula (I) was introduced in the vapor deposition apparatus of FIG. 1. When the evaporation section was gradually heated to a temperature of 120 to 160 (C while maintaining at a vacuum of 10 to 75 mTorr (1.33 to 10.0 Pa), the evaporation material vaporized into the dimer gas, and the source gas was thereby formed. Next, source gas was introduced in the decomposition section that had been heated to 600 (C, and in this decomposition section, the source gas introduced was thermally decomposed into the monomer gas by the scheme as described above. The resulting monomer gas was then introduced in the deposition section which had been maintained at a vacuum of 63.7 mTorr (8.5 Pa) at the maximum. The thus introduced monomer gas polymerized on the surface of the polystyrene substrate placed in the deposition section by the scheme as described above to form the polymer layer. The polymer layer formed had an average thickness of 0.8 (m. The steps of the polymer layer formation as described above were conducted in nitrogen atmosphere to prevent oxidizing of the formyl group in the evaporation material and the polymer layer. Accordingly, the chamber after the completion of the vapor deposition was promptly filled with nitrogen gas.

(2) Formation of Schiff Base

20% (percent by weight) aqueous solution of polyallylamine (Polyallylamine-L (20%) manufactured by Nittobo) was heated at a vacuum of about 40 to 60 mmHg (5.32 to 7.98 kPa) and a temperature of 100° C. to thereby remove the water content by distillation. After adding ethanol, the mixture was refluxed with heating and dissolved to produce a 0.1% ethanol solution of polyallylamine. This solution was filled in a polystyrene dish formed with the polymer layer as described above to bring the polymer layer formed in the interior surface of the dish with the polyallylamine. After leaving at room temperature for 2 hours, the solution in the dish was decanted, and the dish was dried overnight at a reduced pressure at a temperature of about 70° C. As a consequence of the procedure as described above, polyallylamine Schiff base of the polymer represented by the formula (II) was formed on the interior surface of the polystyrene dish (see the scheme as described above), and the interior of the dish was fully washed with distilled water to remove the polyallylamine that failed to react.

Next, the dish was immersed in a solution of 1% SBH/denatured alcohol (ethanol 90%, methanol 10%) at room temperature for 2 hours for reduction treatment. The dish was then fully washed with distilled water, and dried in an oven at an inner temperature of about 60° C. for 2 hours. The cell culture substrate was produced as described above by using the 0.1% solution of polyallylamine in ethanol. This dish was designated Sample No. 1.

This polyallylamine (alkyl-containing polymer) is compound (3) as mentioned above, and has a weight average molecular weight of 10,000. This polyallyamine is commercially available from Nittobo with the product name of PAA-L. The resulting Schiff base polymer was the one as shown below.

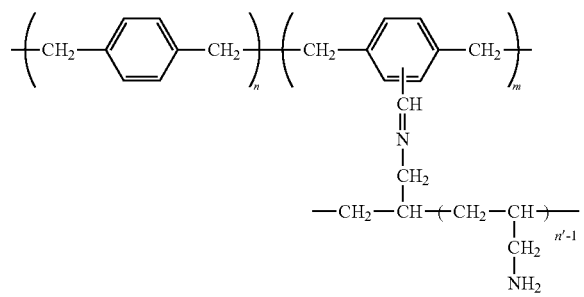

The procedure as described above was repeated except that the polyallyamine was used at a concentration in ethanol of 0.01% to produce Sample No. 2, and Sample Nos. 3 and 4 were similarly prepared by using the polyallyamine at a concentration in ethanol of 0.001% and 1%, respectively. The substrate coated with collagen (Sample No. 5) was also prepared.

Example 2

Rat Hepatocyte Primary Culture

The sample substrate Nos. 1 to 4 and No. 5 prepared in Example 1 were used in the cultivation test of the rat normal hepatocyte.

The cells inoculated were primary culture of the mature rat hepatocyte. The hepatocyte was isolated from 5 to 9 week old male Wister rat (conventional or clean, Std, purchased from Sankyo Labo Service Corporation) by collagenase perfusion. The hepatocyte was inoculated at the inoculation density of $4 \times 10^4$ cells/cm$^2$ to the culture medium as described below, and the condition of the cell culture was visually confirmed after 6 hours, 2 days, and 4 days.

The culture mediums used were Dulbecco's Modified Medium (DMEM) manufactured by Kojin Bio supplemented with 2-[4-(2-Hydroxyethyl)-1-piperadinyl]ethanesulfonic acid (HEPES) (final concentration, 20 mM; manufactured by Dojindo Co., Ltd.), Essential Amino Acid (NEAA) (final concentration, 0.1 mM; manufactured by Gibco), penicillin (final concentration 100 units/ml; manufactured by Wako, Osaka, Japan), streptomycin (final concentration, 100 g/ml; manufactured by Sigma), amphotericin B (final concentration, 0.25 g/ml; manufactured by Sigma) further with additional ingredients of $10^{-7}$M of insulin (manufactured by Wako, Osaka, Japan), $10^{-7}$M of dexamethasone (manufactured by Sigma), $10^{-8}$M of epidermal growth factor (EGF) (manufactured by Takara), $10^{-6}$M of Zn (heavy metal), $10^{-7}$M of Cu, $10^{-7}$M of Mn, and $10^{-8}$M of Se.

FIGS. 1 to 5 show the condition of Sample Nos. 1 to 5 after 6 hours; FIGS. 6 to 10 show the condition of Sample Nos. 1 to 5 after 2 days; FIGS. 11 to 15 show the condition of Sample Nos. 1 to 5 after 4 days.

The cells cultivated on each sample were also evaluated by CYP1A1/2 activity test.

Concentration of resorufin (R) which is a metabolite of ethoxyresorufin (ER) was calculated on the bases of absorbance and fluorescence intensity which was used as an index of the enzymatic activity of the metabolic enzyme (CYP1A1/2). In addition, enzyme inducibility of 3-methylcholanthrene (3MC) was evaluated by dissolving the 3-methylcholanthrene (3MC) in the culture medium and exposing the cell to the 3-methylcholanthrene (3MC). CYP1A catalyses O-dealkylation reaction (EROD, ethoxyresorufin-O-deethylation) of ethoxyresorufin (ER) to produce resorufin (a fluorescent substance). Ethoxyresorufin solution which is a fluorescent substrate was added to the culture medium, and after the exposure for a certain period, a part of the culture medium was collected and diluted with ethanol to measure absorption of the residual ethoxyresorufin and fluorescence intensity of the newly produced resorufin.

First, the culture medium as described above having 0.5 μM of 3MC added (+3MC) and not added (−) were prepared as a pretreatment so as to realize two conditions, namely, the condition with the induction and the condition without such induction. After cultivating the cells in these culture mediums for 2 days, the cells were exposed to culture medium having added thereto 10 μM of ER and 10 μM of dicoumarol, and the incubation was continued for another. 1 hour. The dicoumarol was added to prevent metabolism of the R. The culture medium was then sampled, and dissolved in a solvent such as ethanol to measure the absorbance and the fluorescence intensity. Since the absorbance at 480 nm depends on the residual ER concentration, and the fluorescence intensity at 530-585 nm depends on the concentration of the ER and the R, amount of the R produced was calculated from the data of the absorbance and the fluorescence intensity. Since the fluorescence intensity of the R is by far larger than that of the ER, measurement of the absorbance may be omitted in the cells having some degree of metabolic capacity (Rat normal hepatocyte, HepG2, Caco-2, etc.). These measurement can be readily conducted by using a plate reader such as AP2 microplate system manufactured by Hitachi High-Technologies Corporation. The results are shown in FIG. 16.

After 6 hours of incubation as shown in FIGS. 1 to 5, initial adhesion was favorable in the Comparative Sample No. 5. The initial adhesion was also generally favorable in Sample Nos. 1 and 2. After 2 days of incubation as shown in FIGS. 6 to 10, the growth was sufficient except for Sample Nos. 4 and 1. After 4 days of incubation as shown in FIGS. 11 to 15, formation of spheroids by several cells was noted in Sample Nos. 2, 3, and 5, and this was most significant in Sample Nos. 3 and 5. The growth was also sufficient in Sample No. 1.

Figure 16:
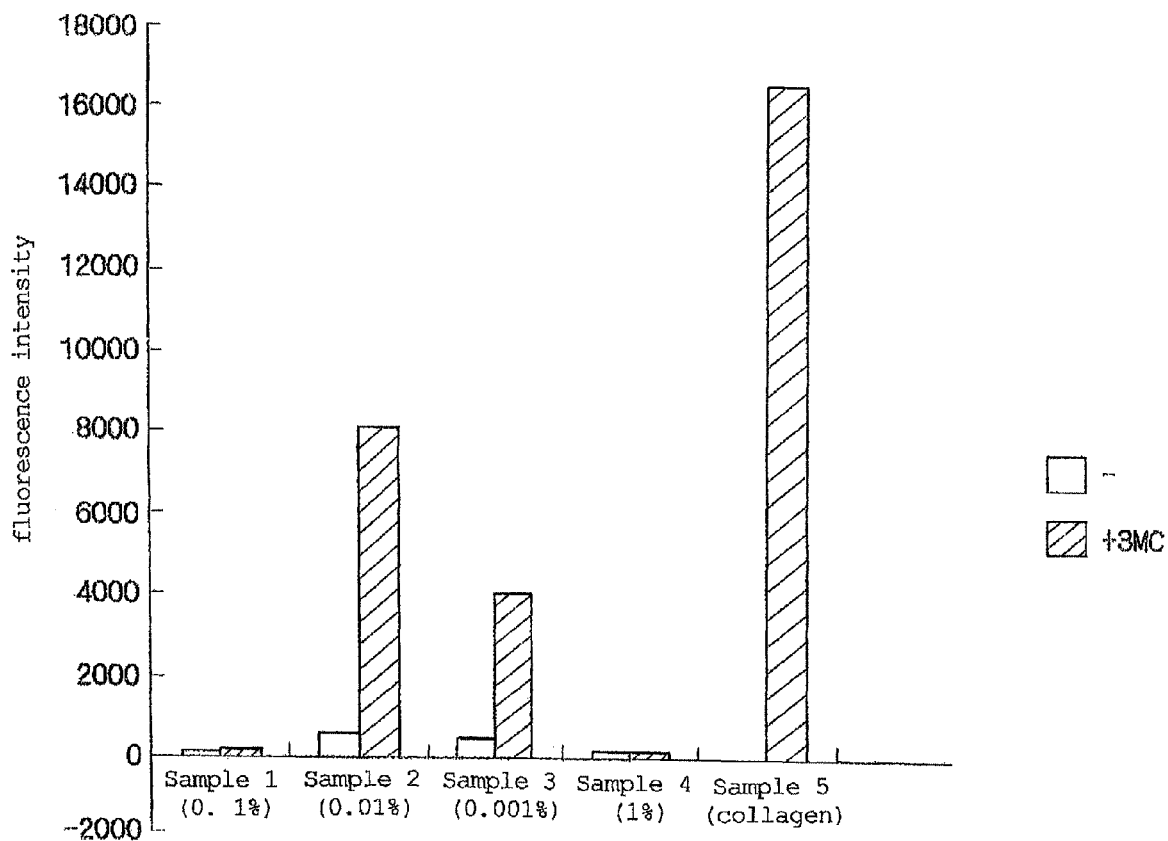
FIG. 16 is a graph showing the result of CYP1A1/2 (an enzyme) activity evaluation for Example 1, Sample No. 1 to 5 after 4 days.
Figure 17:
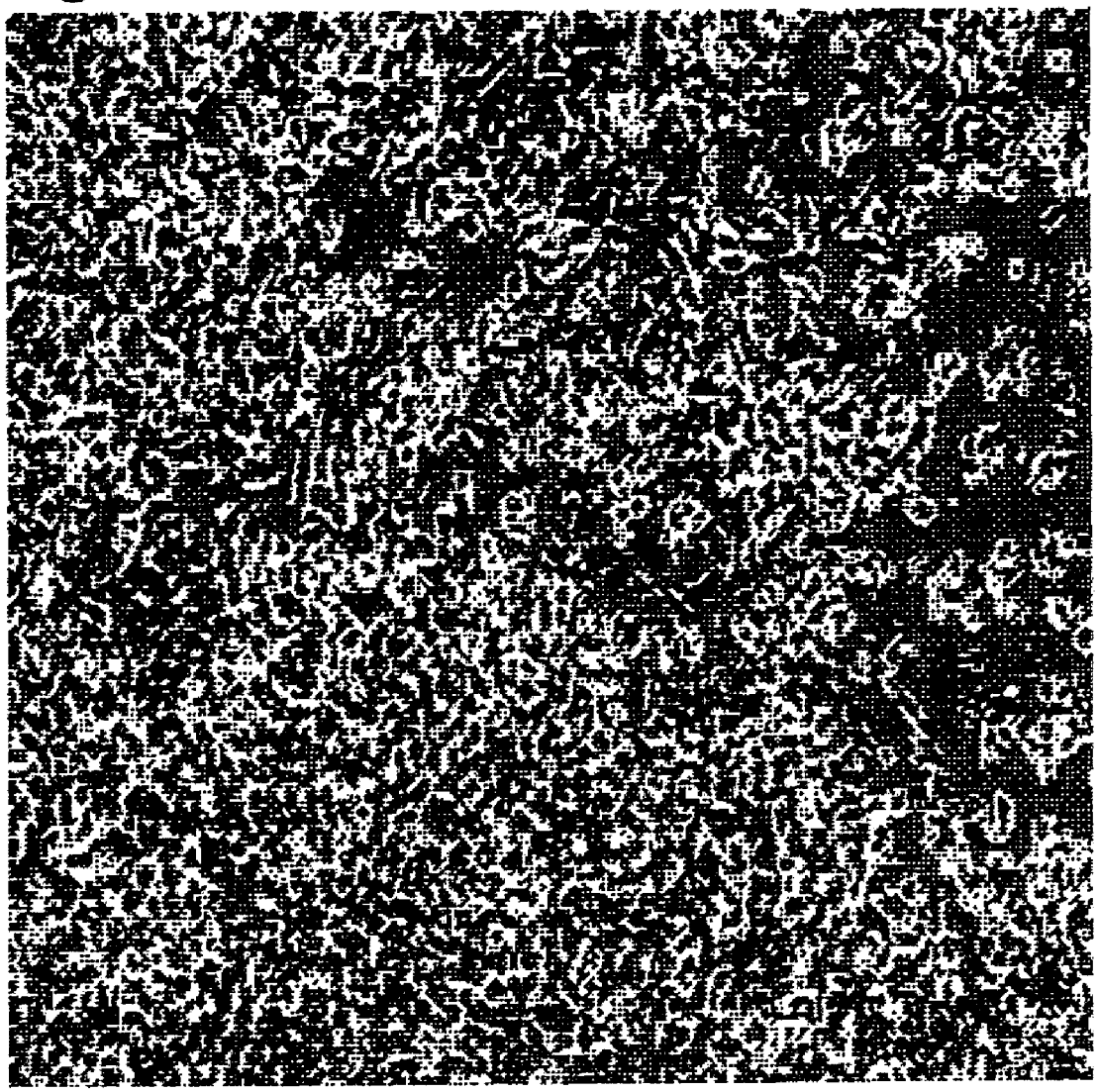
FIG. 17 shows conditions of the culture of Example 2, Sample No. 11 after 1 day.
Figure 18:
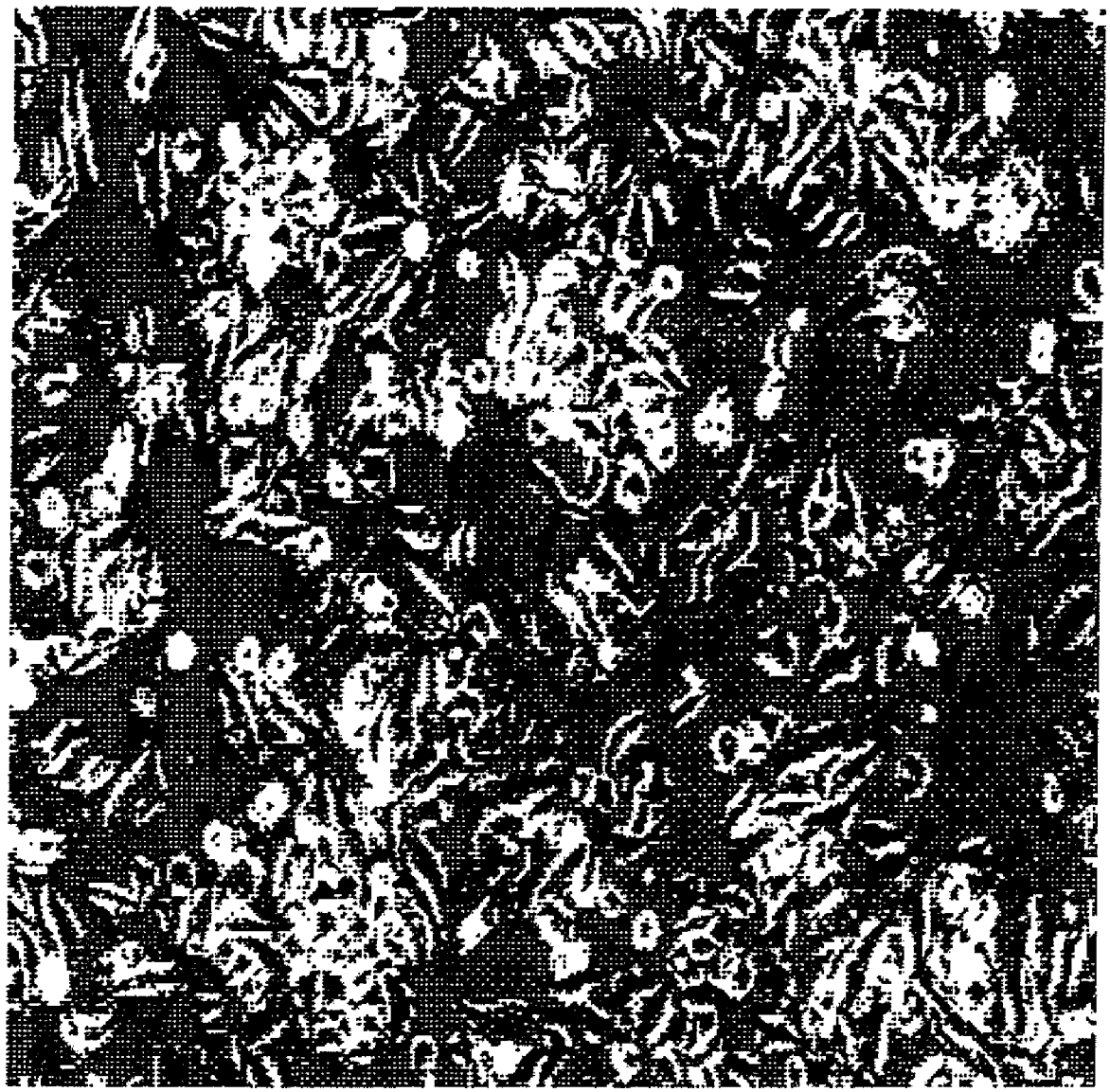
FIG. 18 shows conditions of the culture of Example 2, Sample No. 12 after 1 day.
Figure 19:
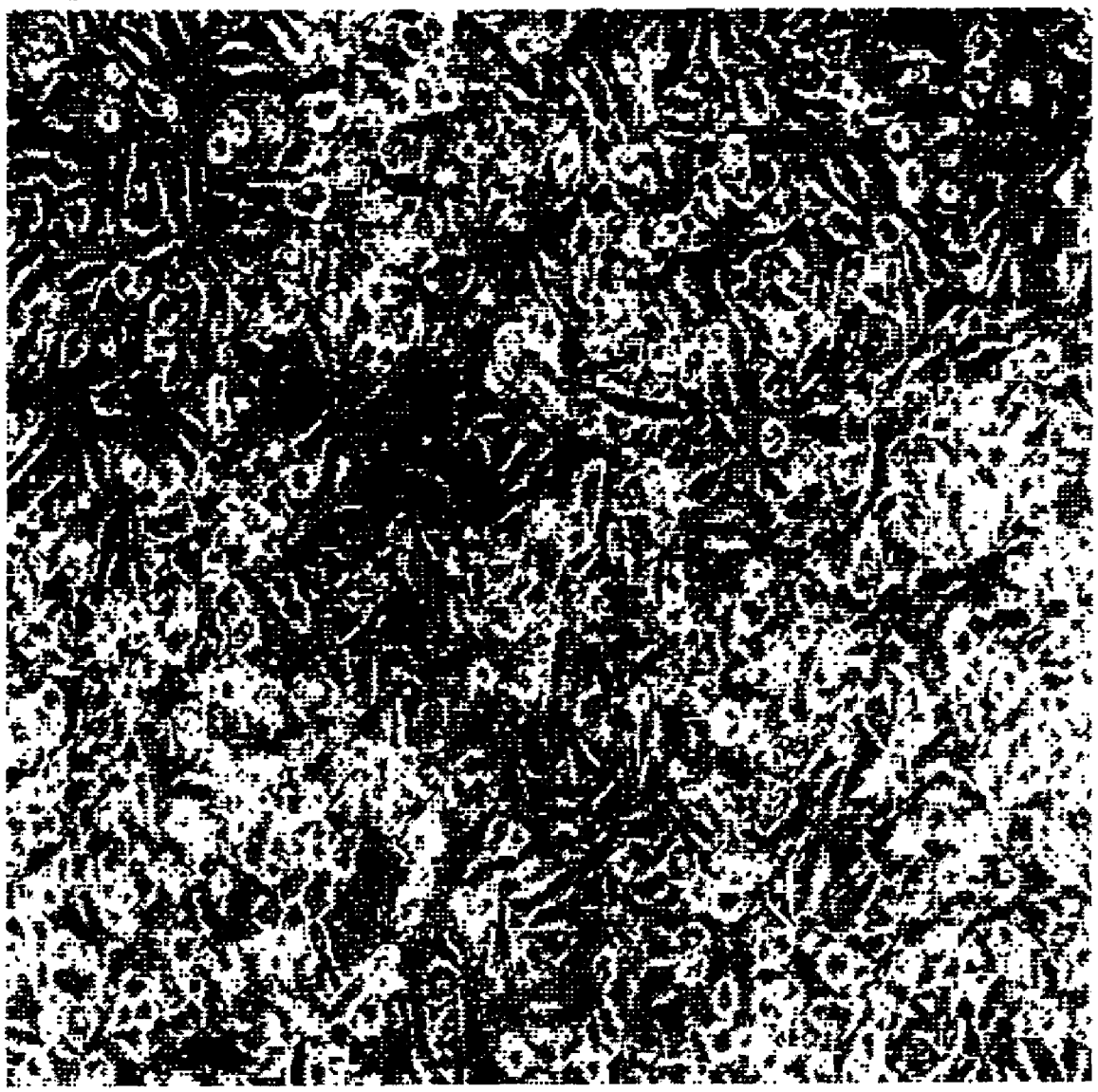
FIG. 19 shows conditions of the culture of Example 2, Sample No. 13 after 1 day.
Figure 20:
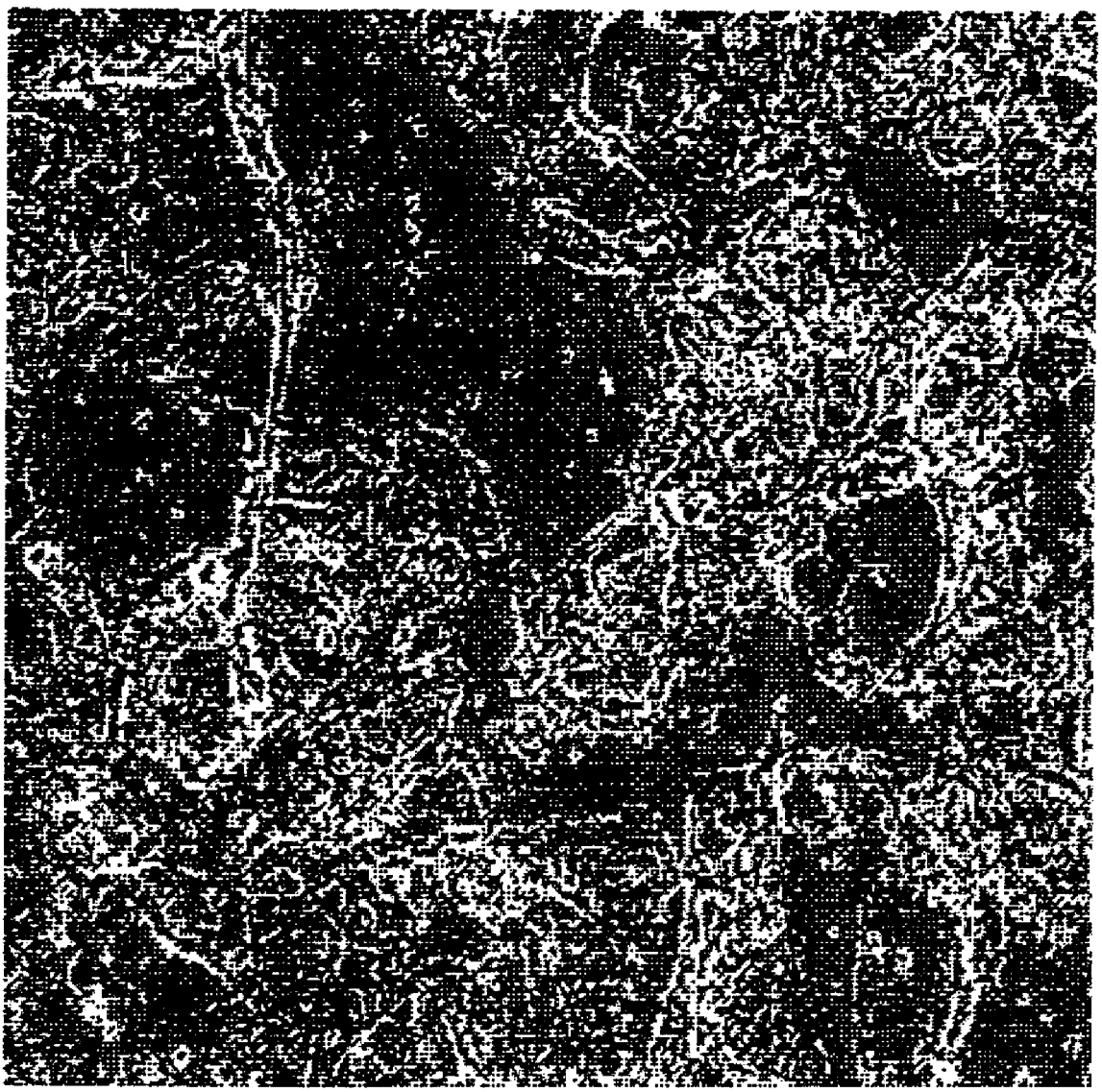
FIG. 20 shows conditions of the culture of Example 2, Sample No. 14 after 1 day.
Figure 21:
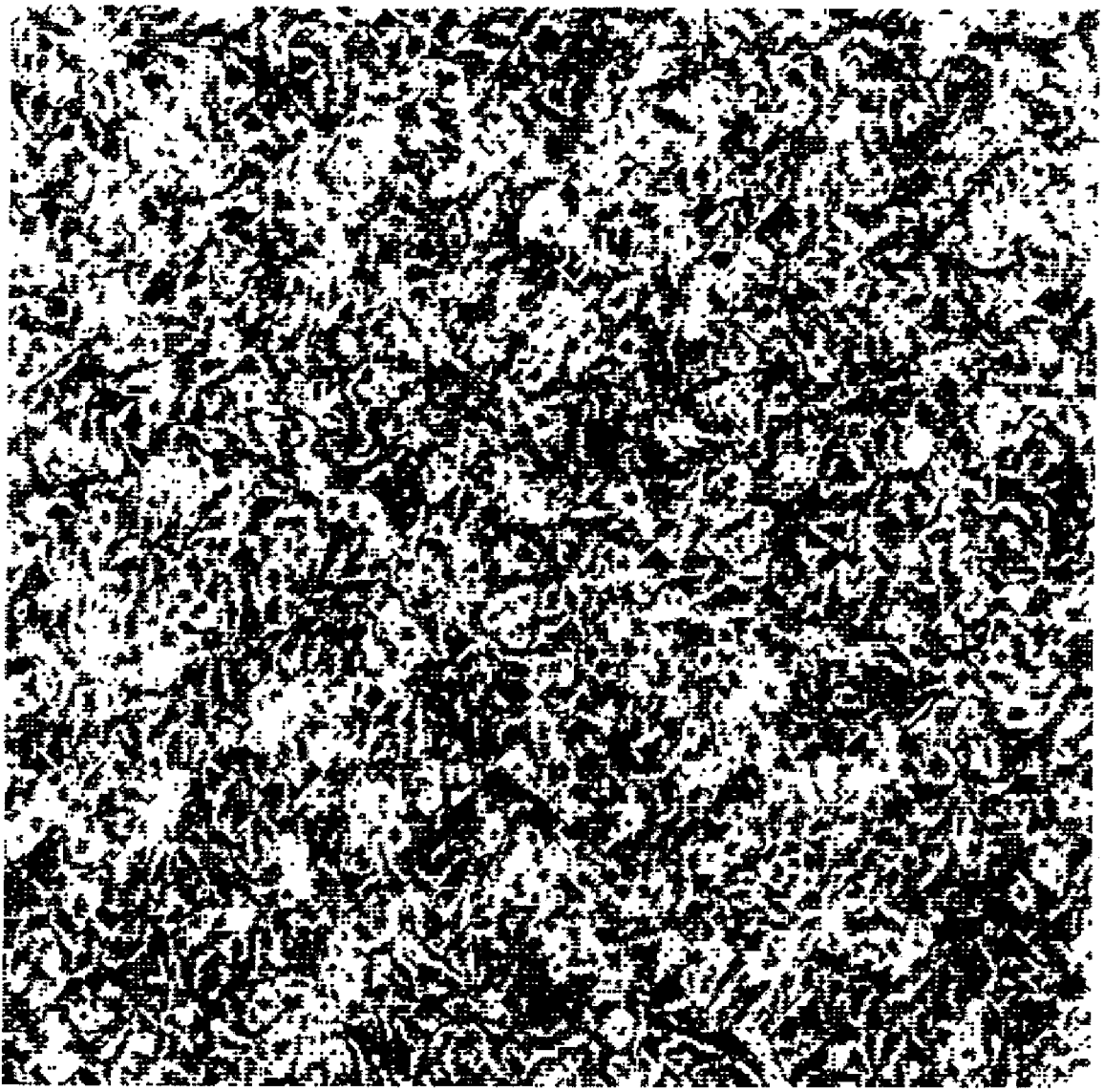
FIG. 21 shows conditions of the culture of Example 2, Sample No. 15 after 1 day.
Figure 22:
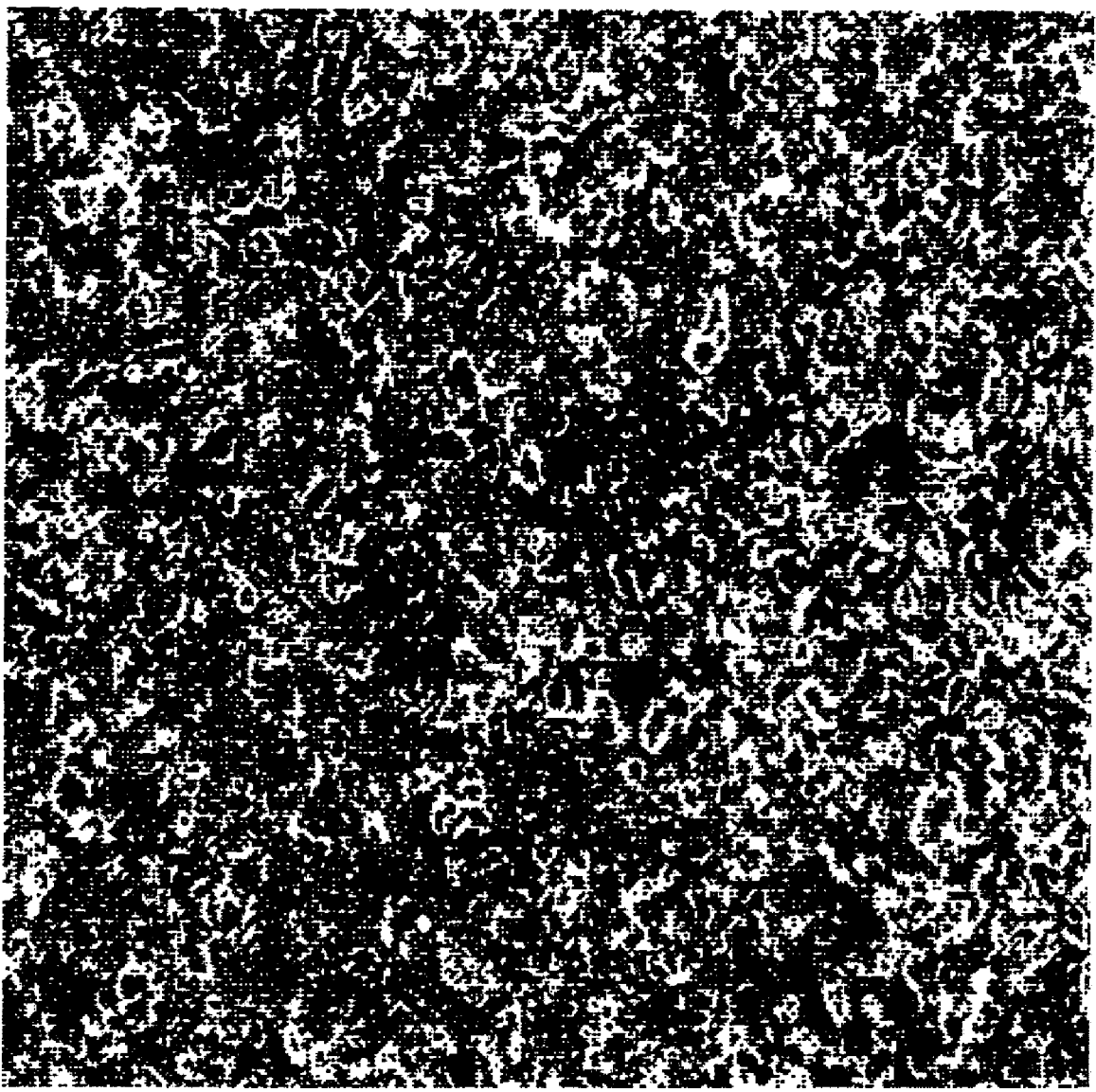
FIG. 22 shows conditions of the culture of Example 2, Sample No. 11 after 7 days.
Figure 23:
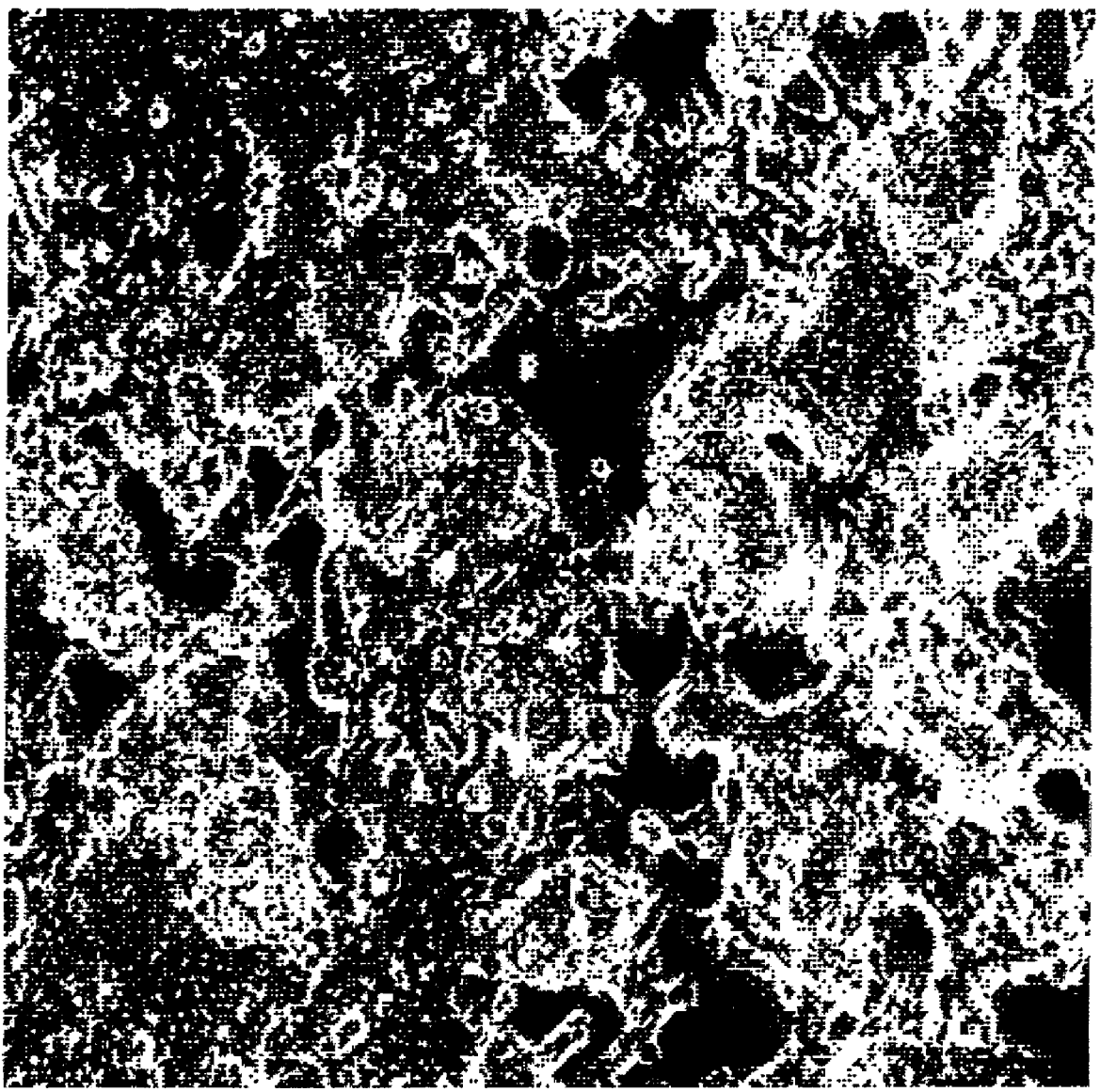
FIG. 23 shows conditions of the culture of Example 2, Sample No. 12 after 7 days.
Figure 24:
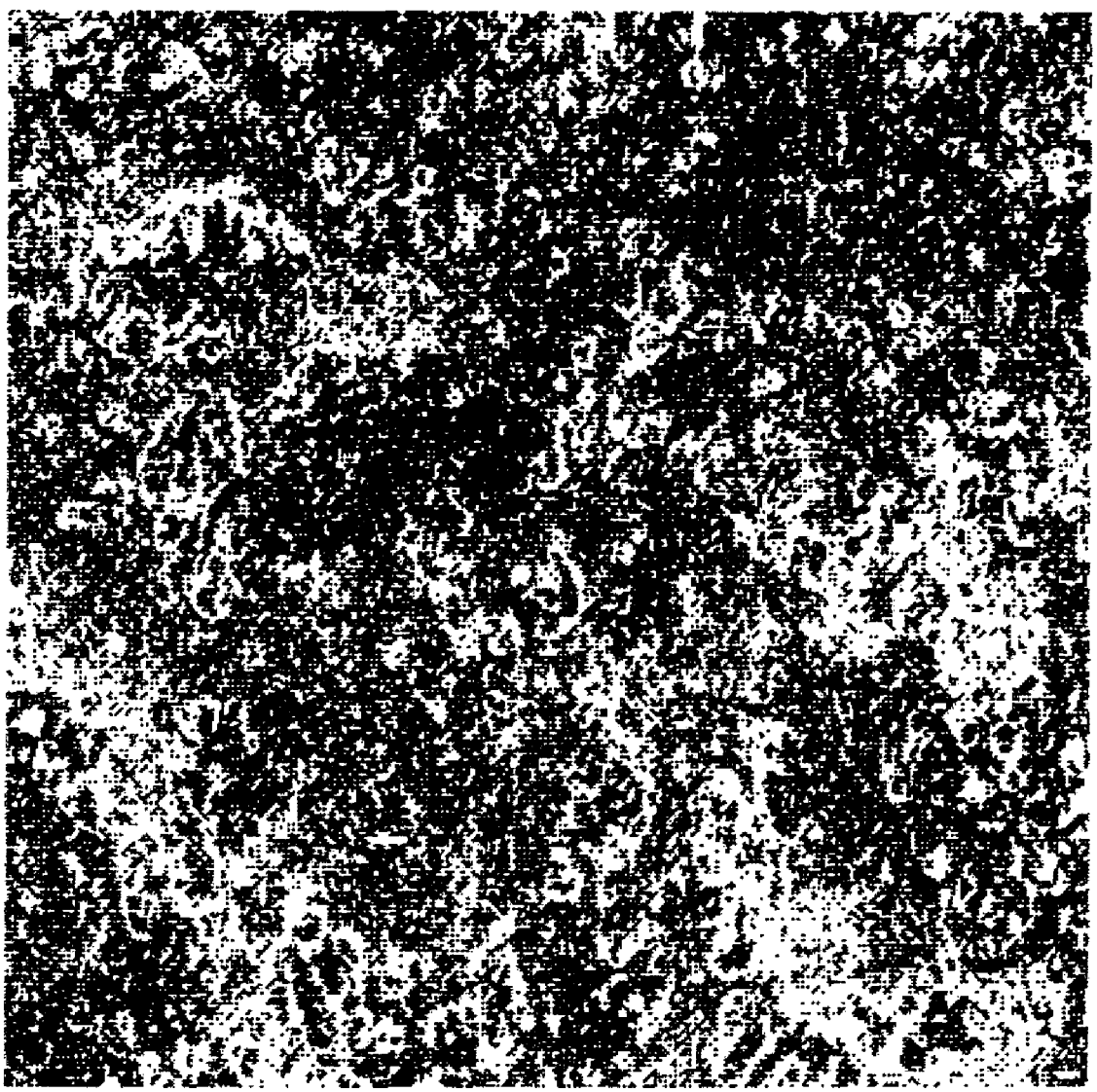
FIG. 24 shows conditions of the culture of Example 2, Sample No. 13 after 7 days.
Figure 25:
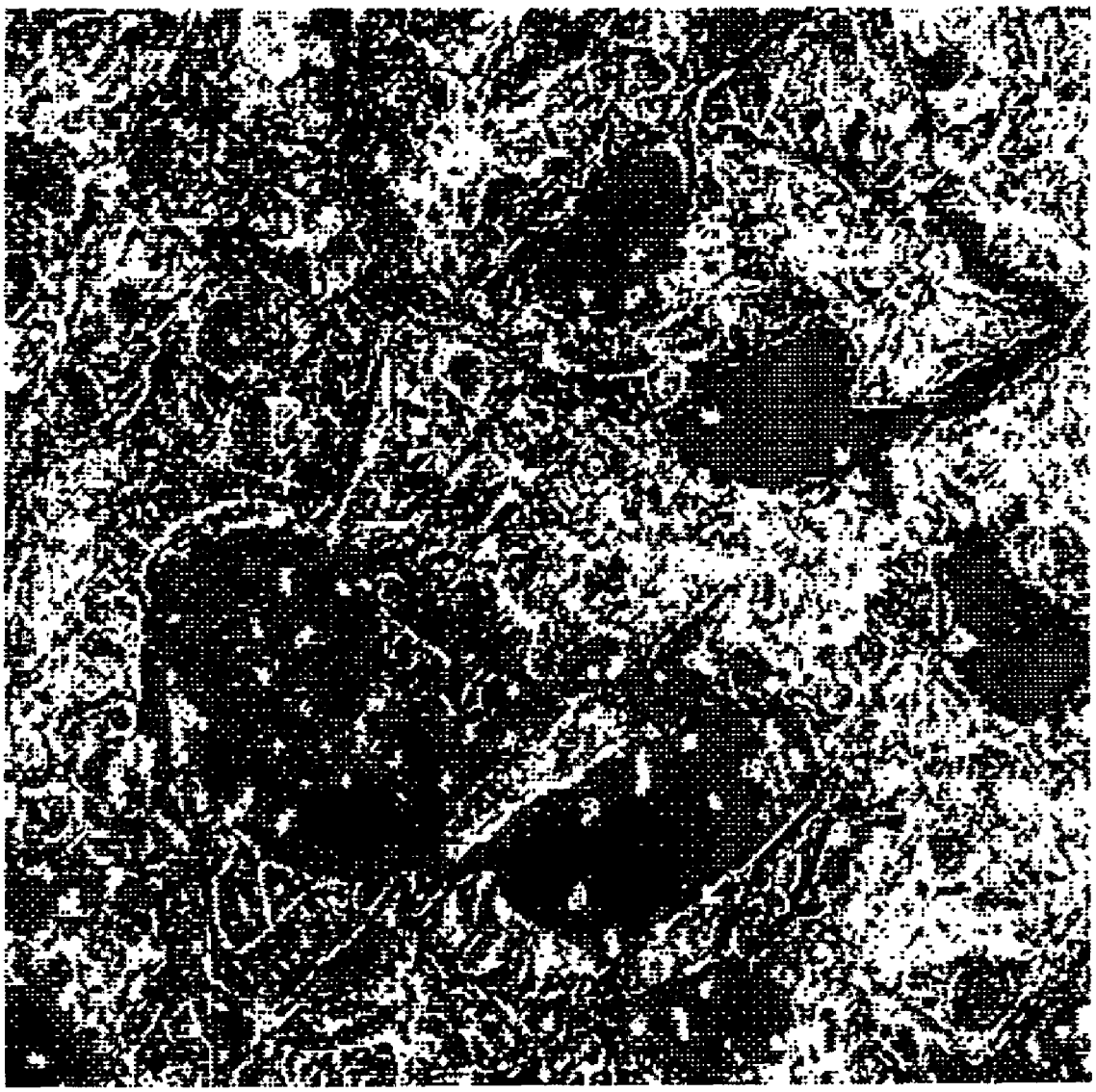
FIG. 25 shows conditions of the culture of Example 2, Sample No. 14 after 7 days.
Figure 26:
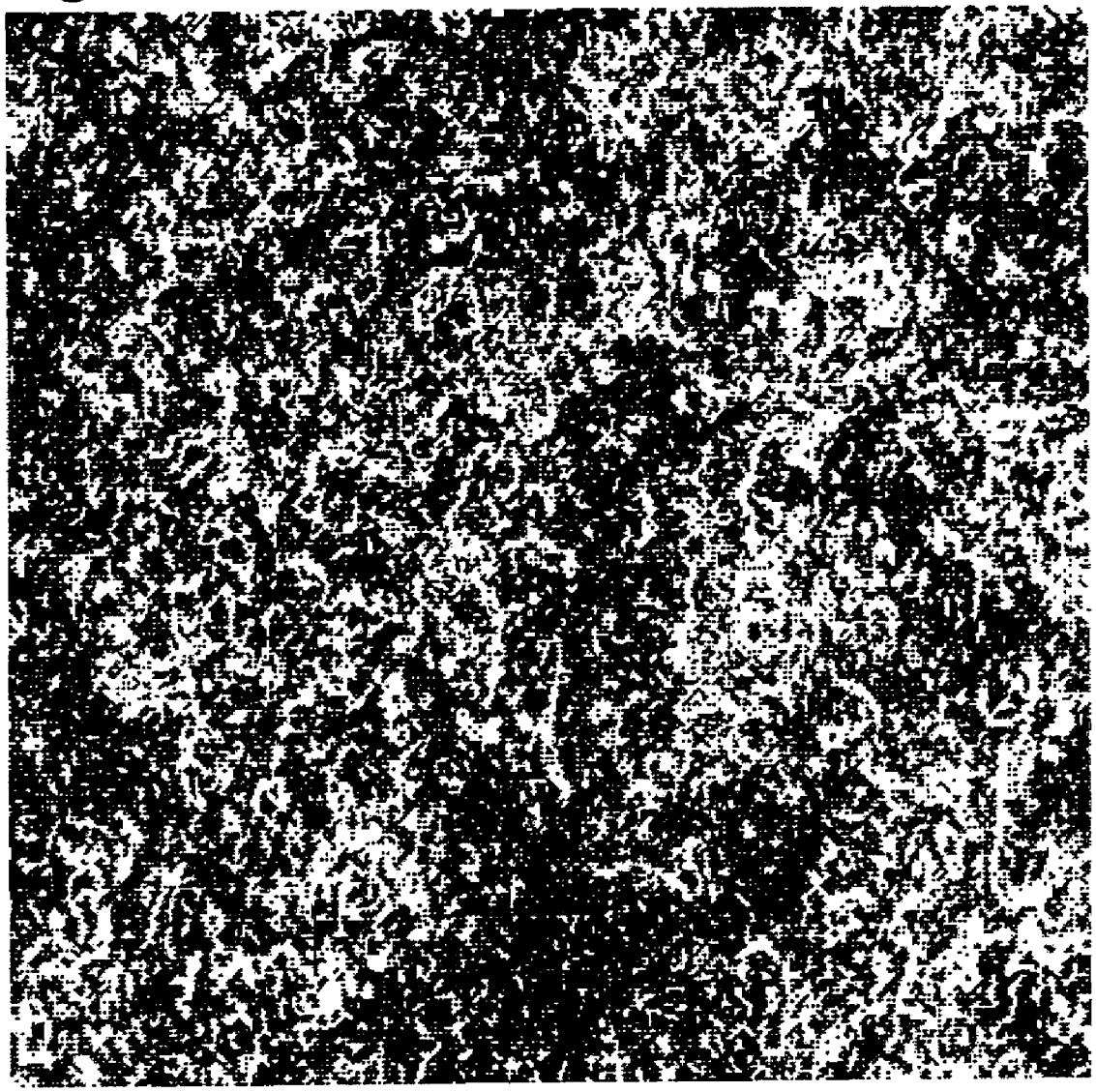
FIG. 26 shows conditions of the culture of Example 2, Sample No. 15 after 7 days.
Figure 27:
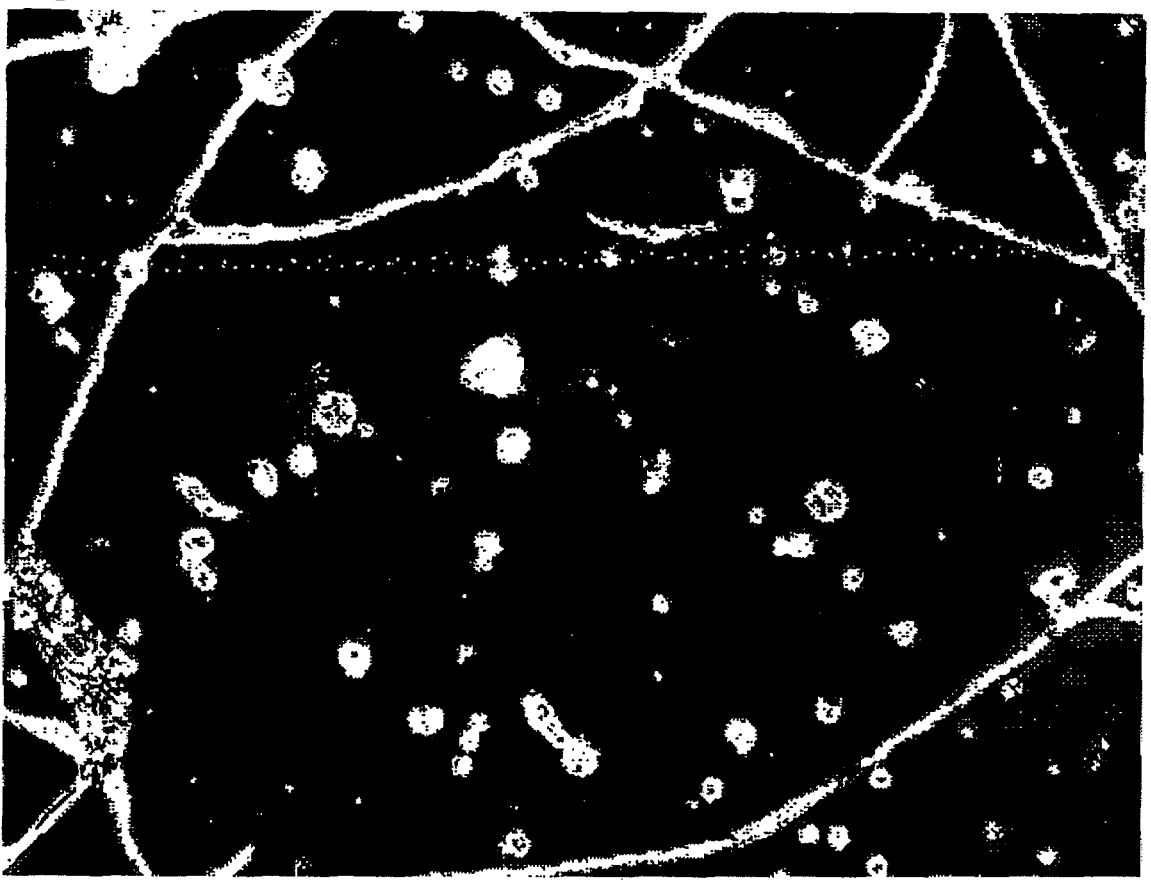
FIG. 27 shows conditions of the culture of Example 3, Sample No. 21 after 1 day.
Figure 28:
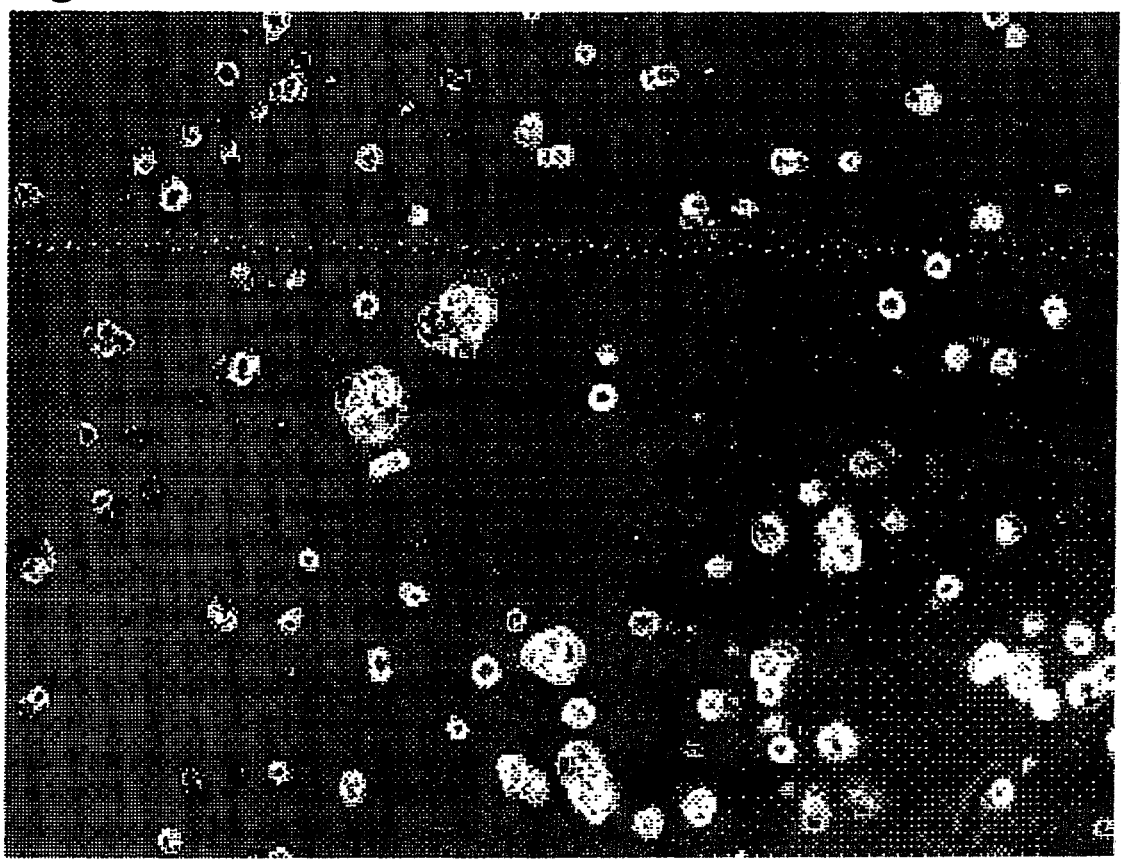
FIG. 28 shows conditions of the culture of Example 3, Sample No. 22 after 1 day.
Figure 29:
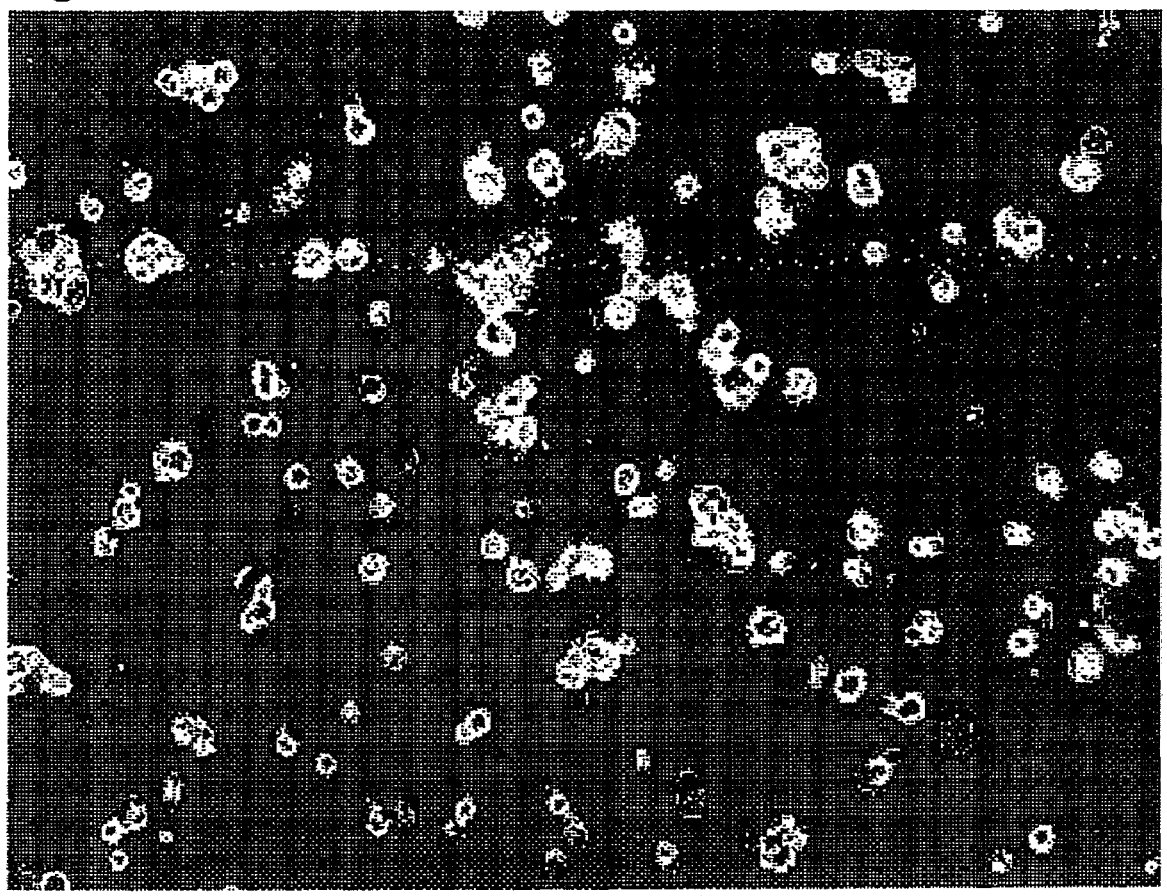
FIG. 29 shows conditions of the culture of Example 3, Sample No. 23 after 1 day.
Figure 30:
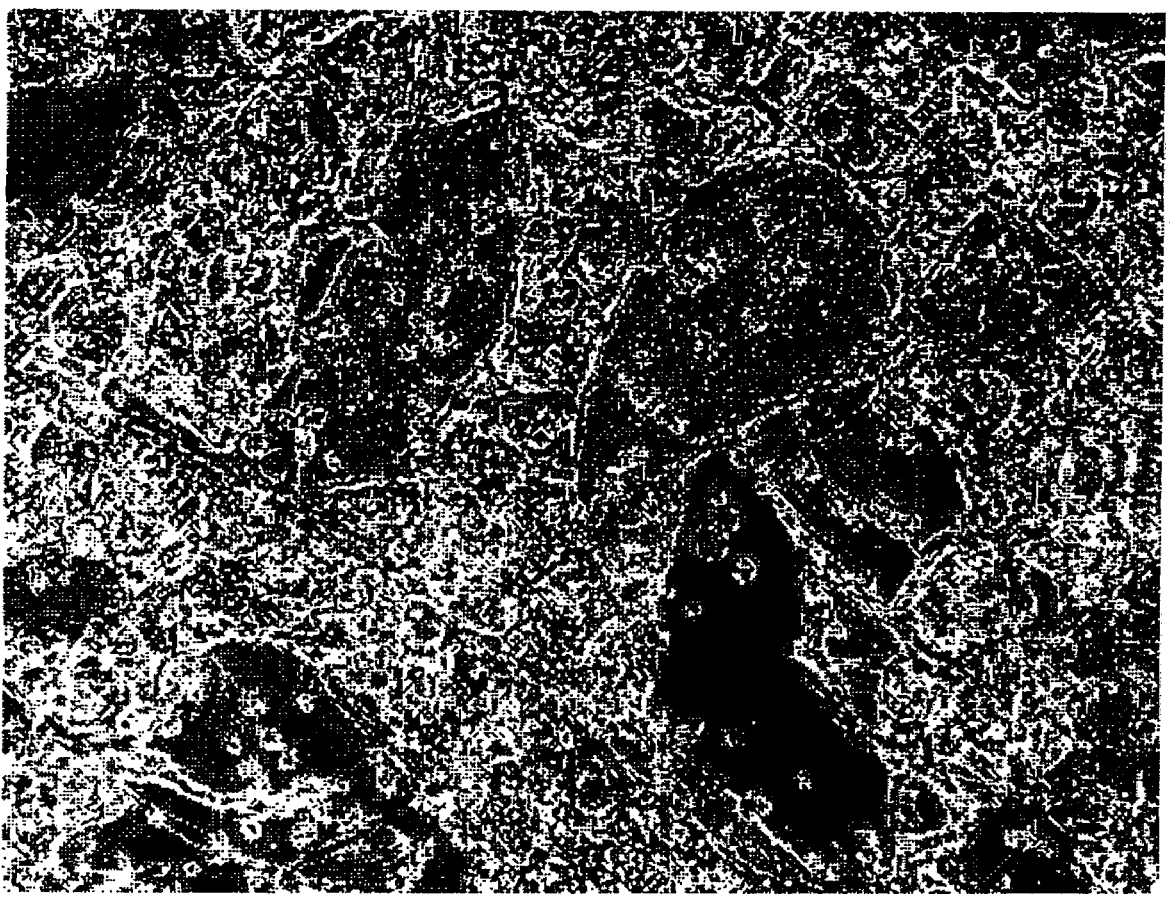
FIG. 30 shows conditions of the culture of Example 3, Sample No. 24 after 1 day.
Figure 31:
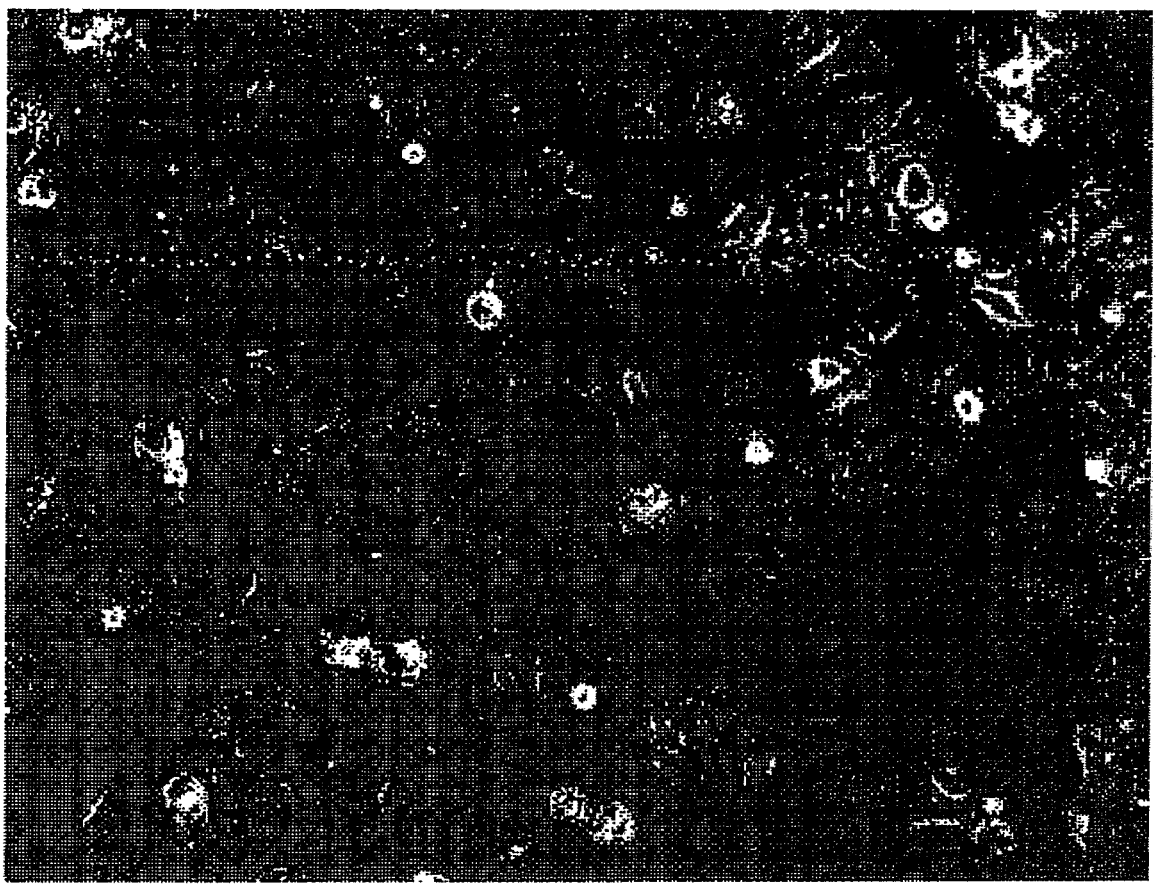
FIG. 31 shows conditions of the culture of Example 3, Sample No. 25 after 1 day.
Figure 32:
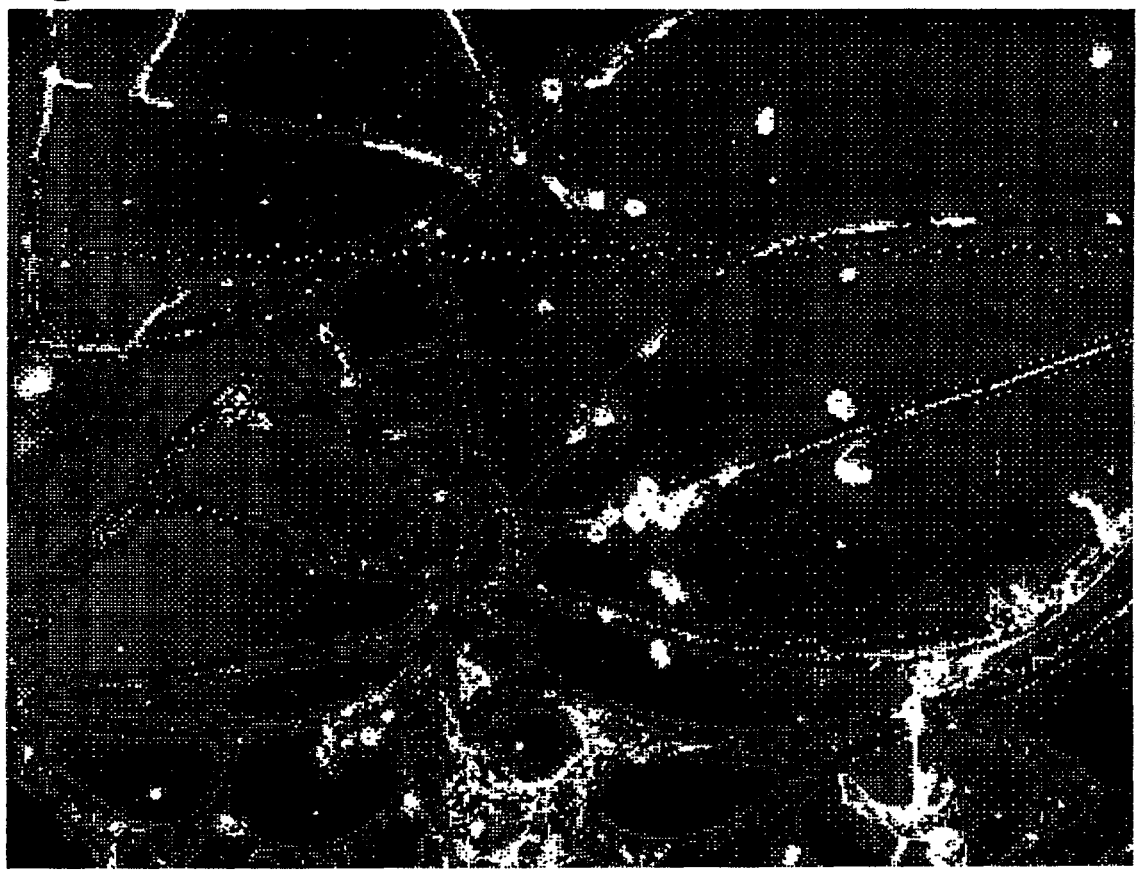
FIG. 32 shows conditions of the culture of Example 3, Sample No. 21 after 3 days.
Figure 33:
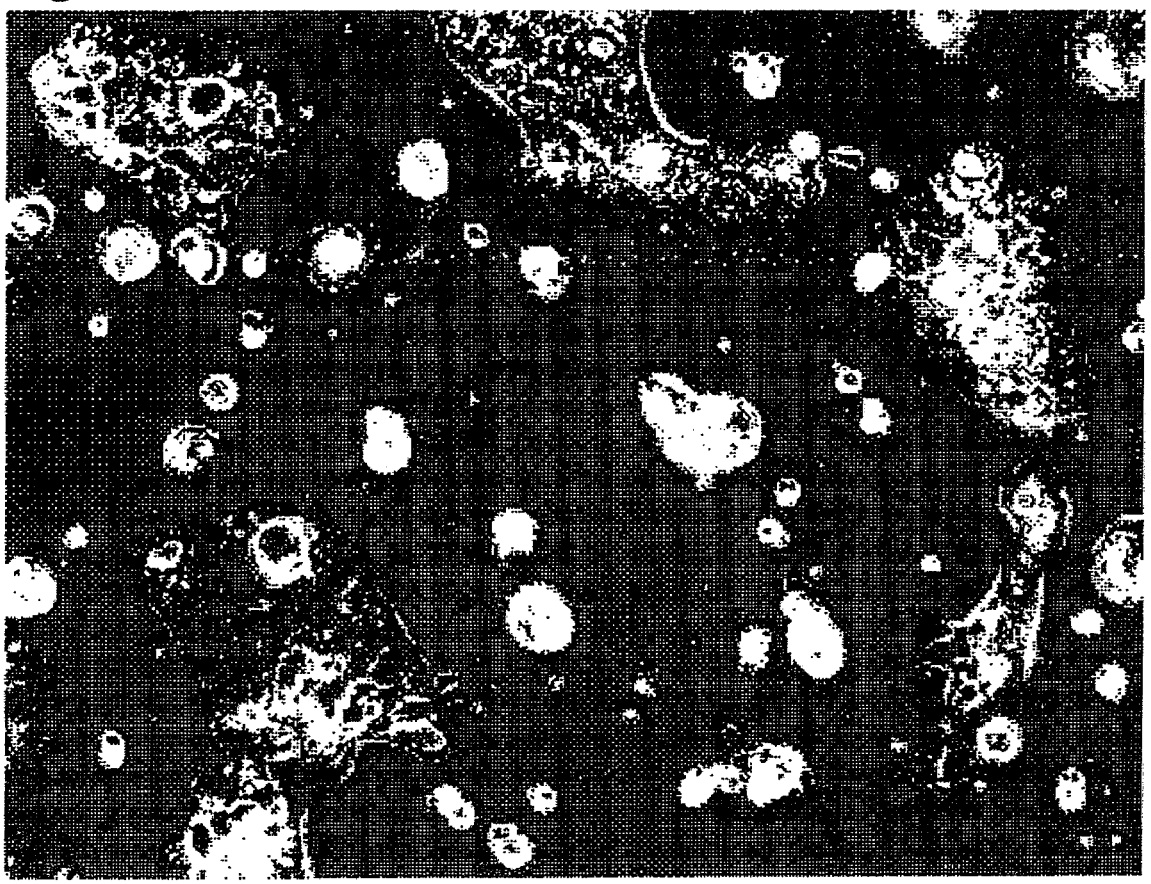
FIG. 33 shows conditions of the culture of Example 3, Sample No. 22 after 3 days.
Figure 34:
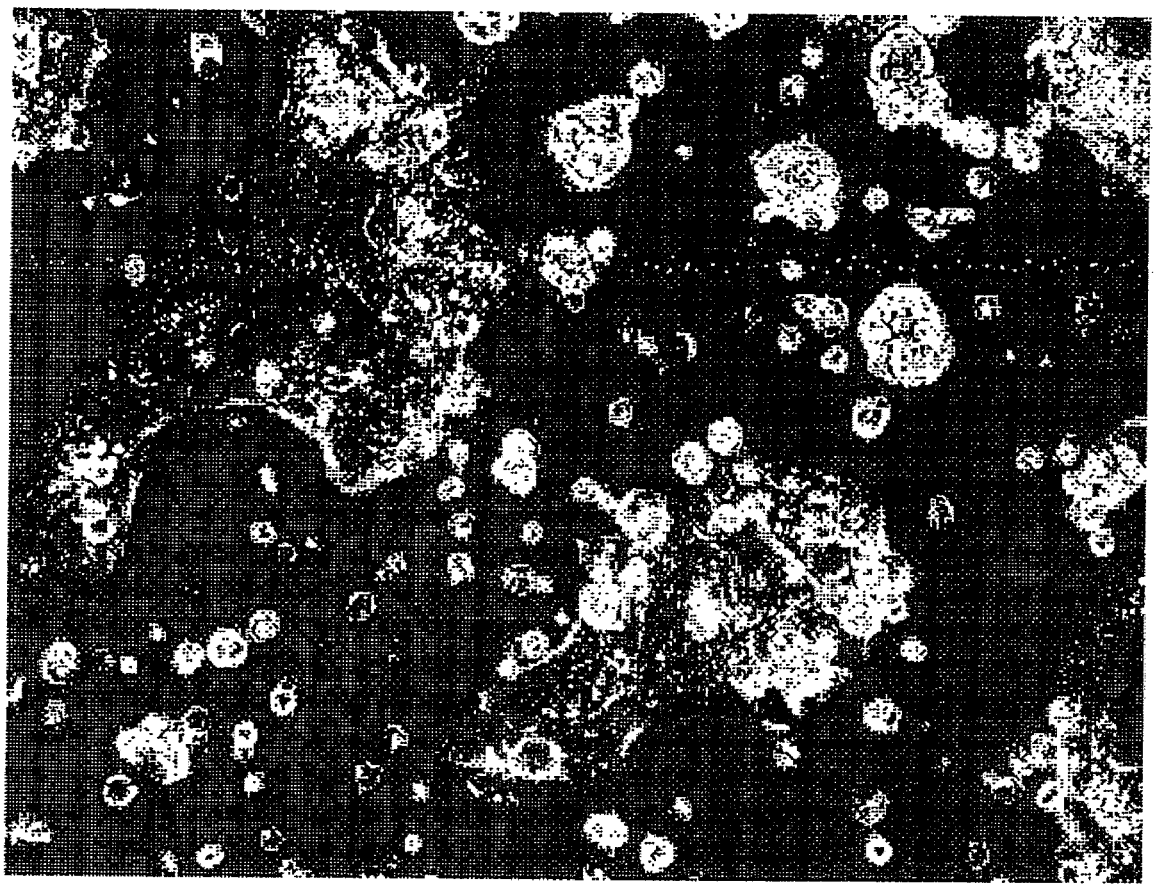
FIG. 34 shows conditions of the culture of Example 3, Sample No. 23 after 3 days.
Figure 35:
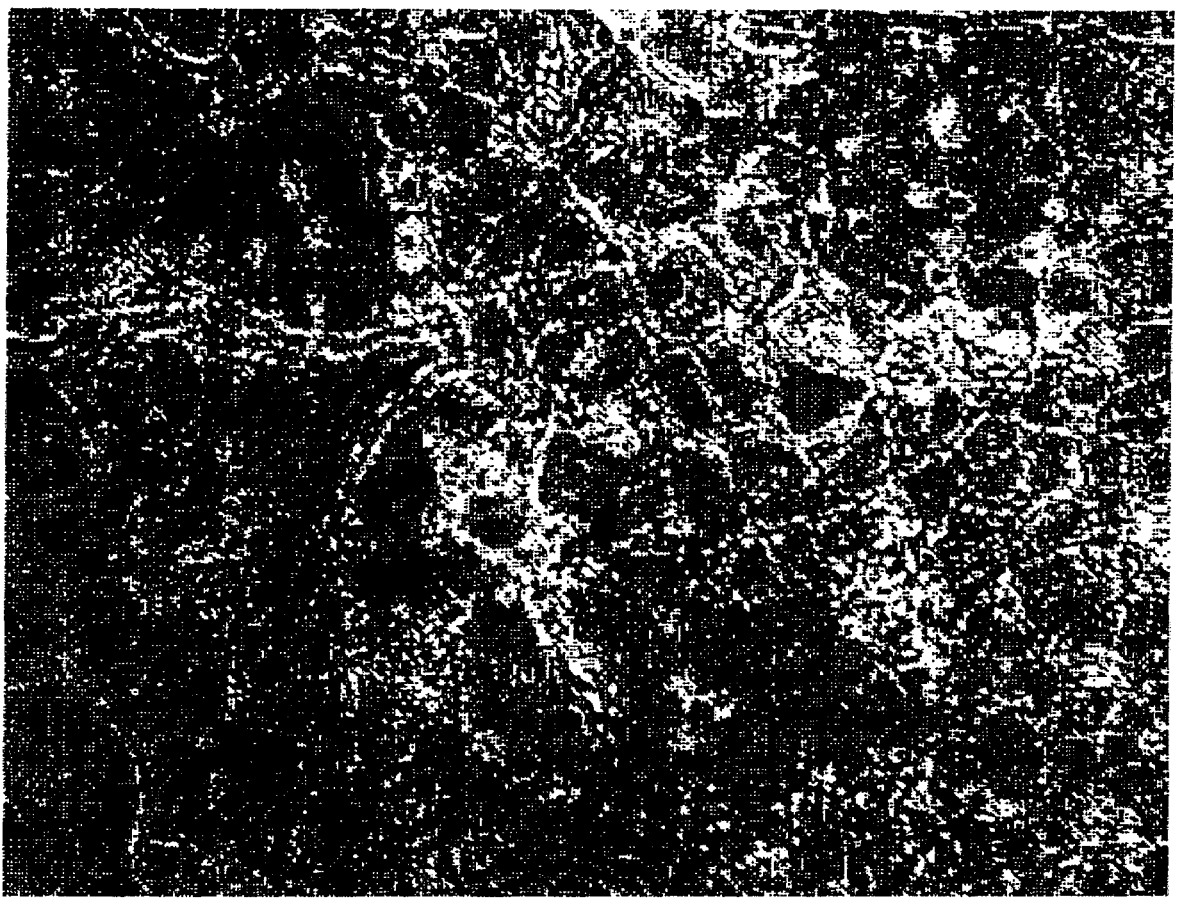
FIG. 35 shows conditions of the culture of Example 3, Sample No. 24 after 3 days.
Figure 36:
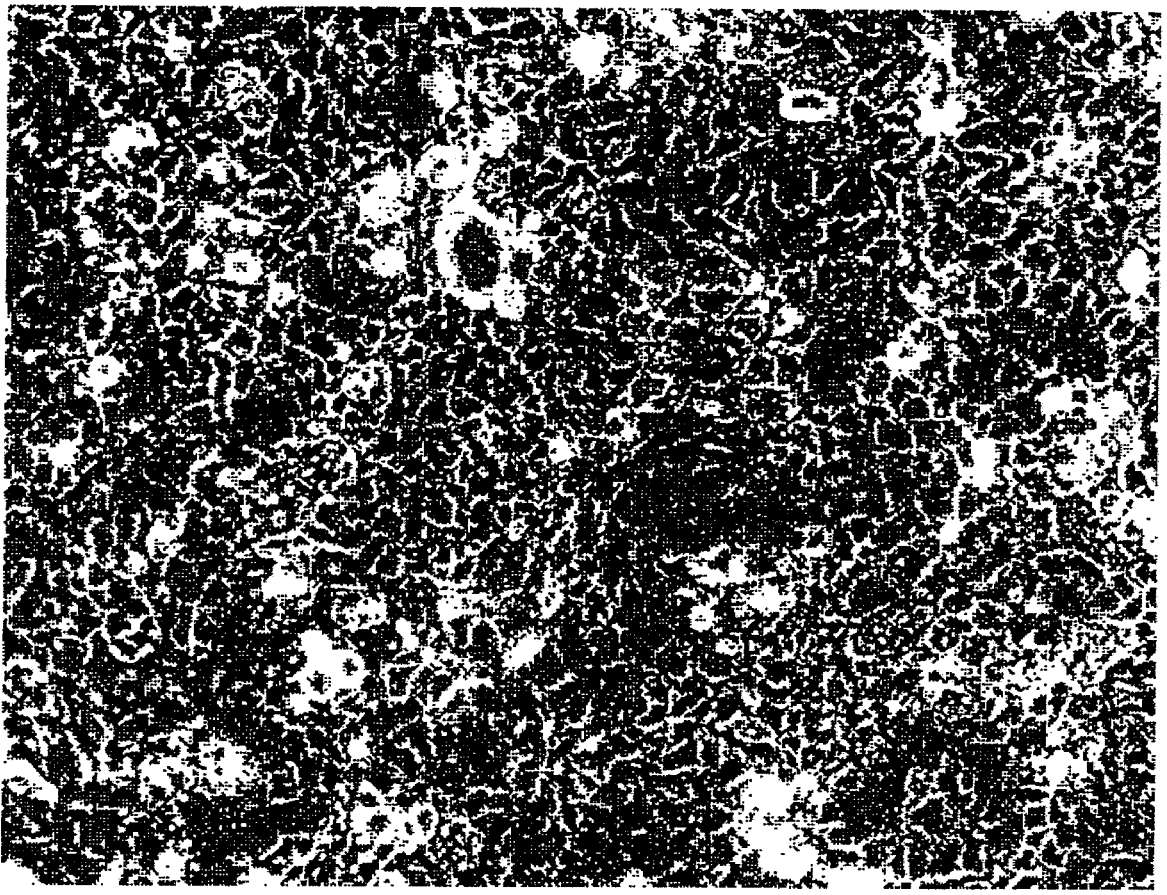
FIG. 36 shows conditions of the culture of Example 3, Sample No. 25 after 3 days.
Figure 37:
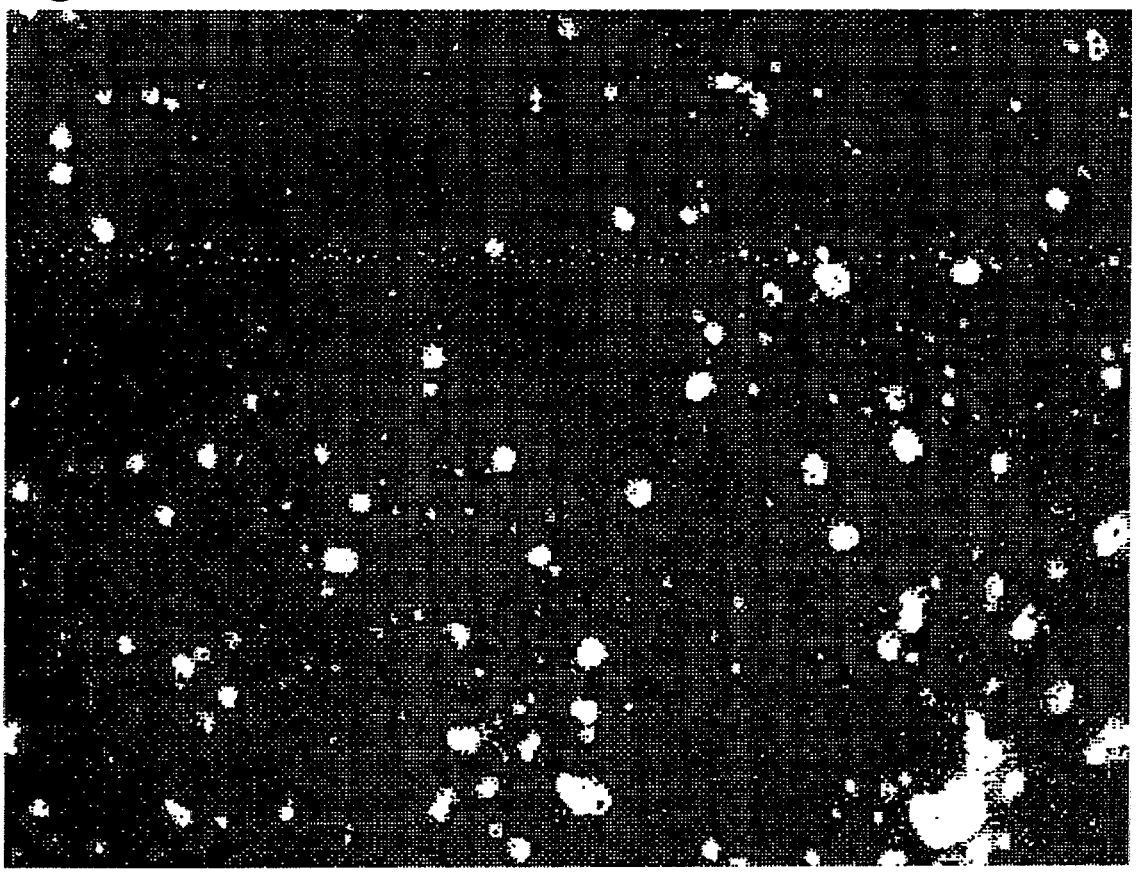
FIG. 37 shows conditions of the culture of Example 3, Sample No. 21 after 5 days.
Figure 38:
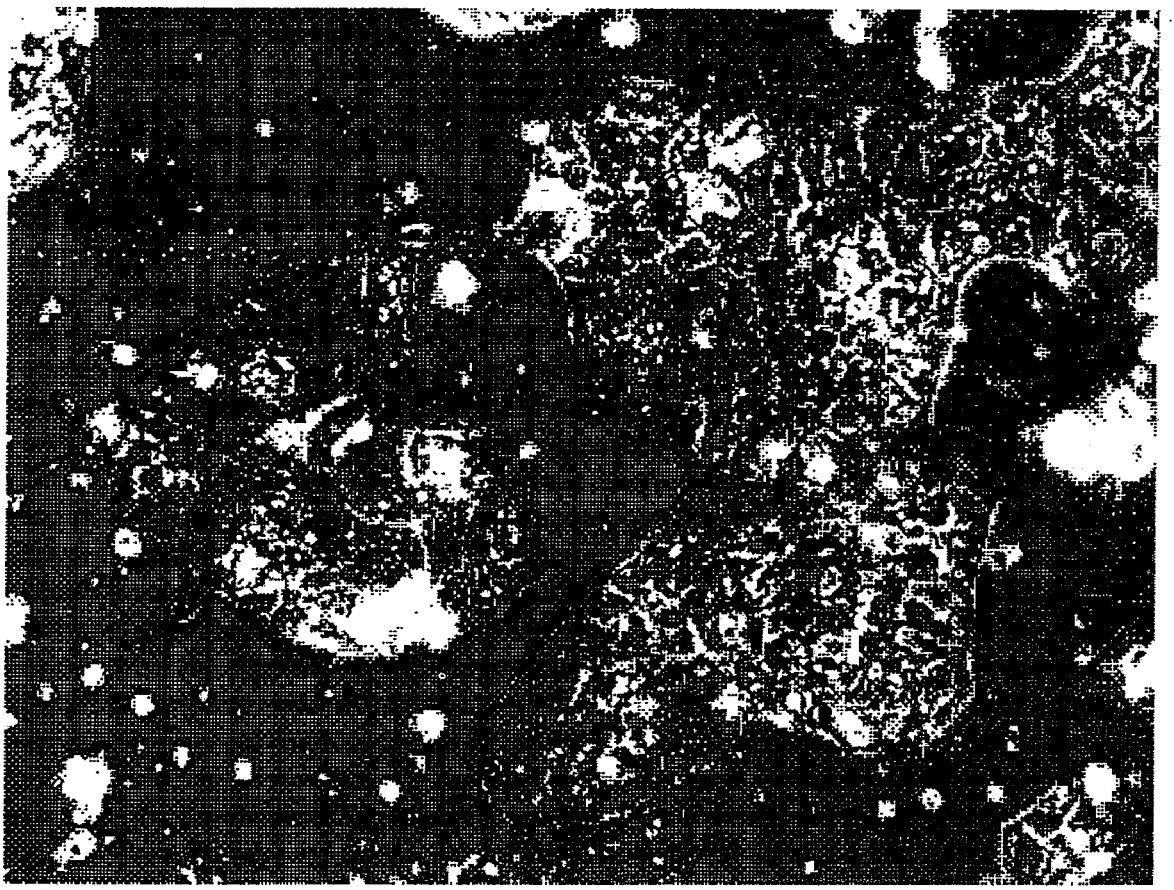
FIG. 38 shows conditions of the culture of Example 3, Sample No. 22 after 5 days.
Figure 39:
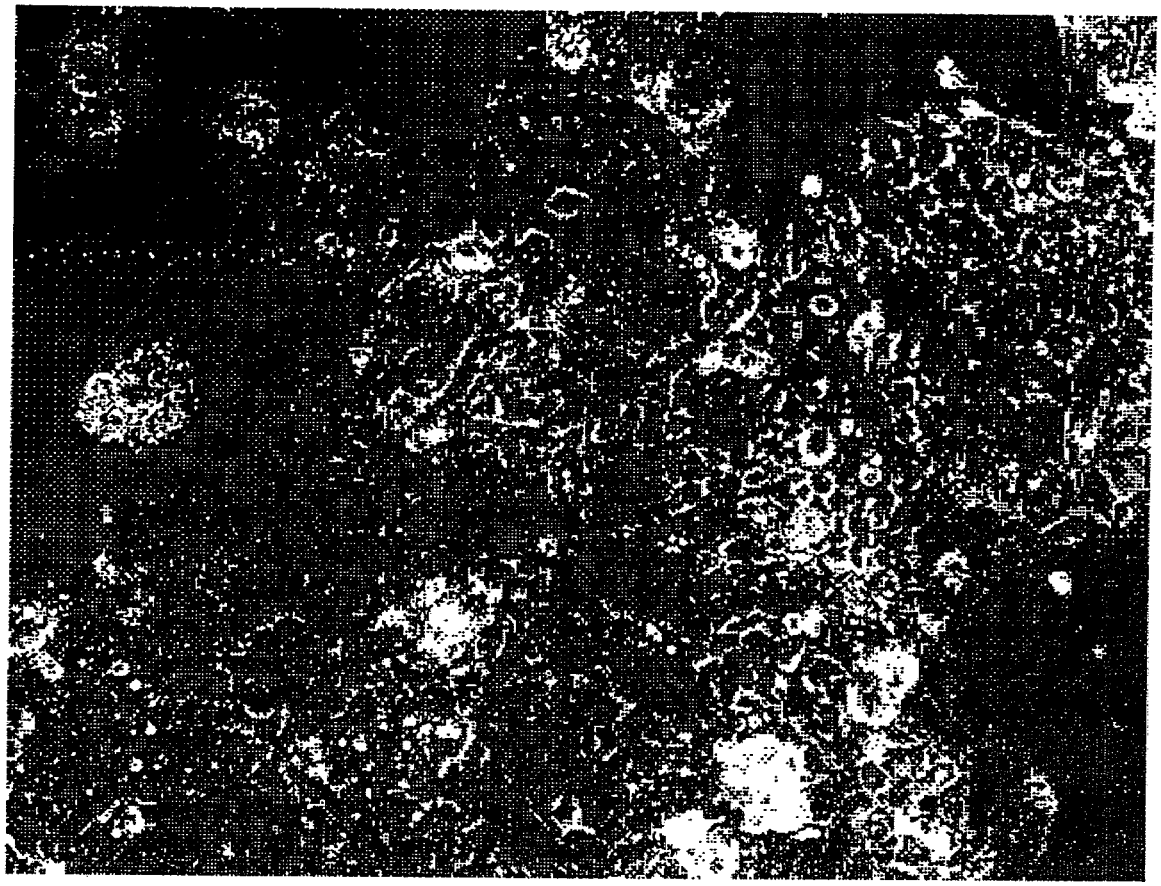
FIG. 39 shows conditions of the culture of Example 3, Sample No. 23 after 5 days.
Figure 40:
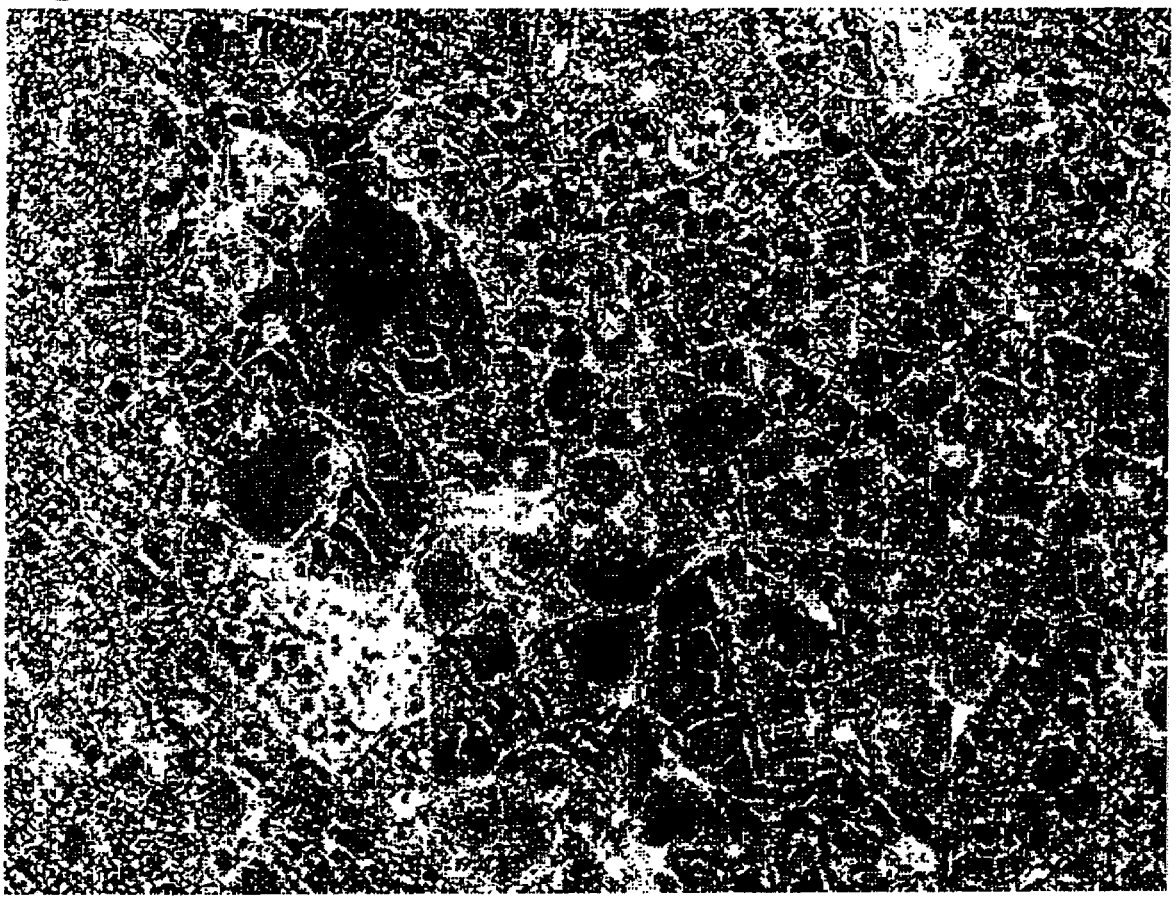
FIG. 40 shows conditions of the culture of Example 3, Sample No. 24 after 5 days.
Figure 41:
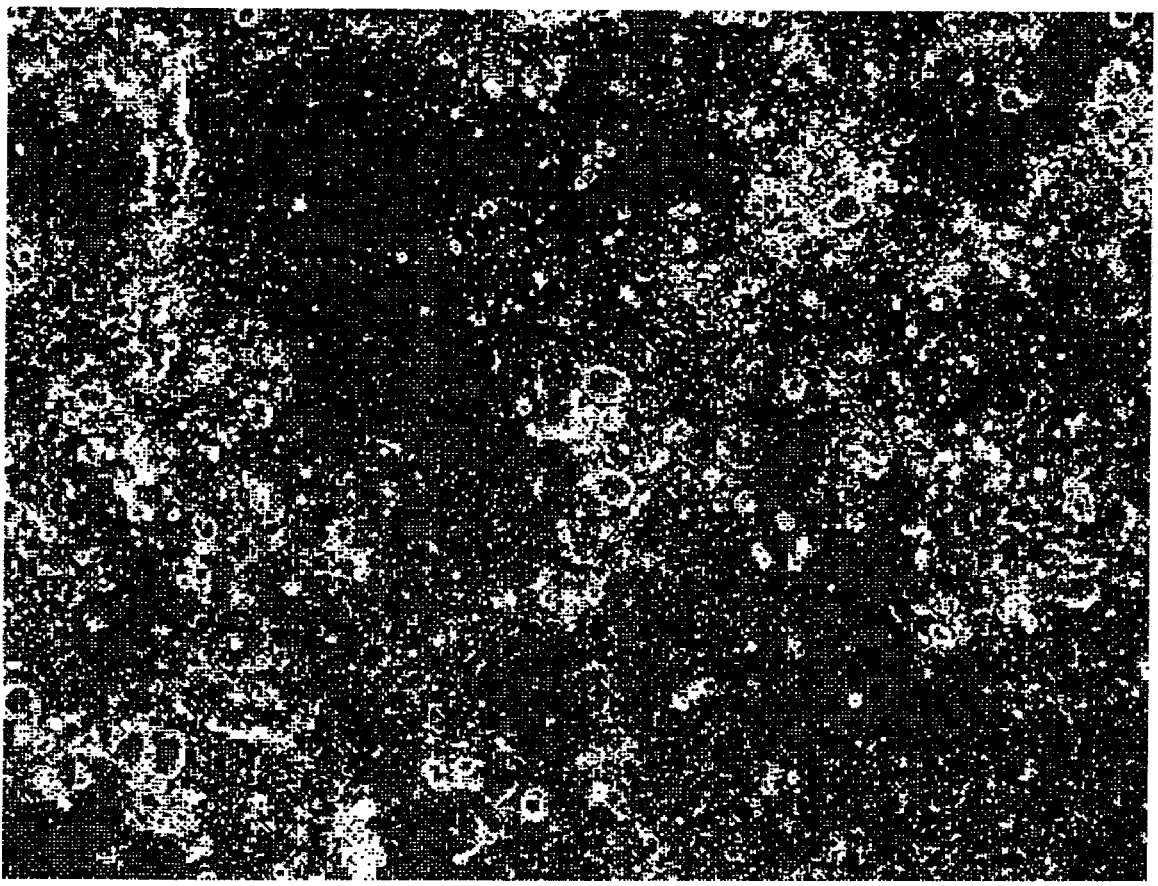
FIG. 41 shows conditions of the culture of Example 3, Sample No. 25 after 5 days.
Figure 42:
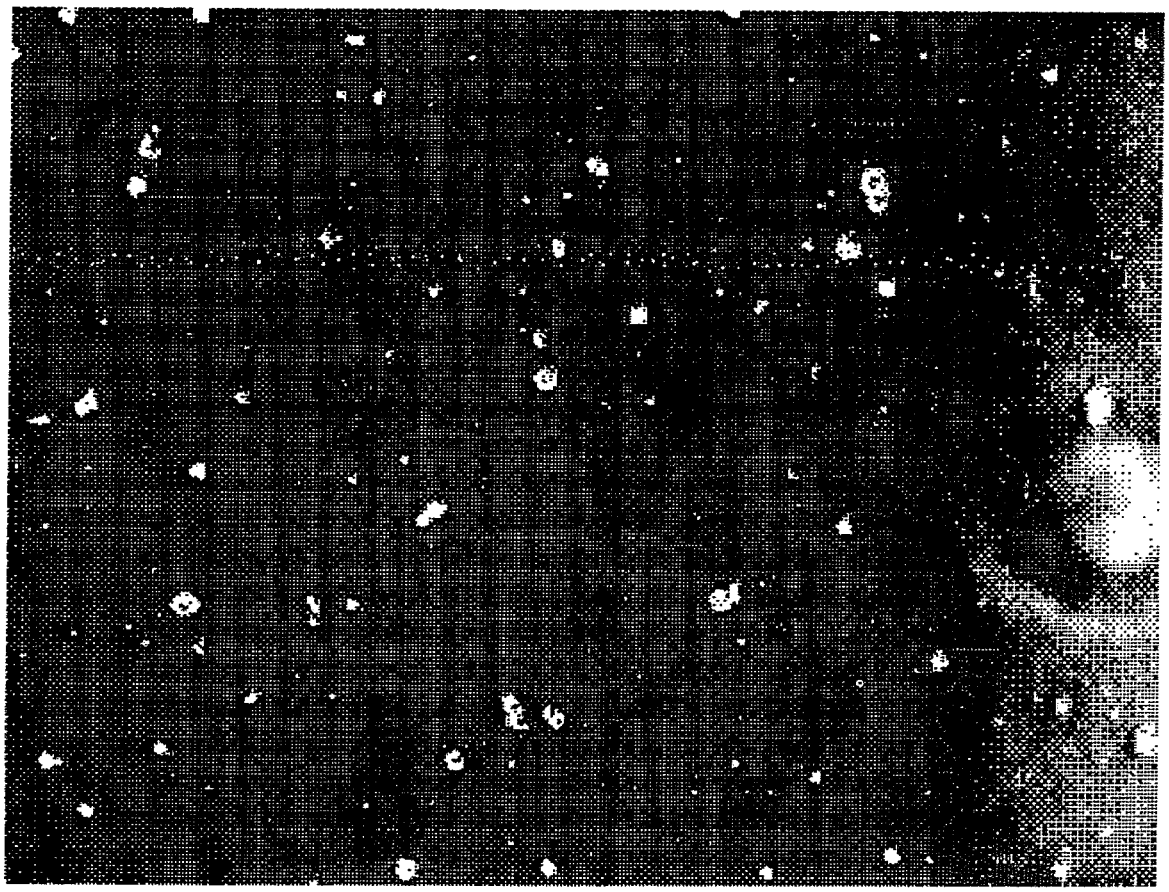
FIG. 42 shows conditions of the culture of Example 3, Sample No. 21 after 7 days.
Figure 43:
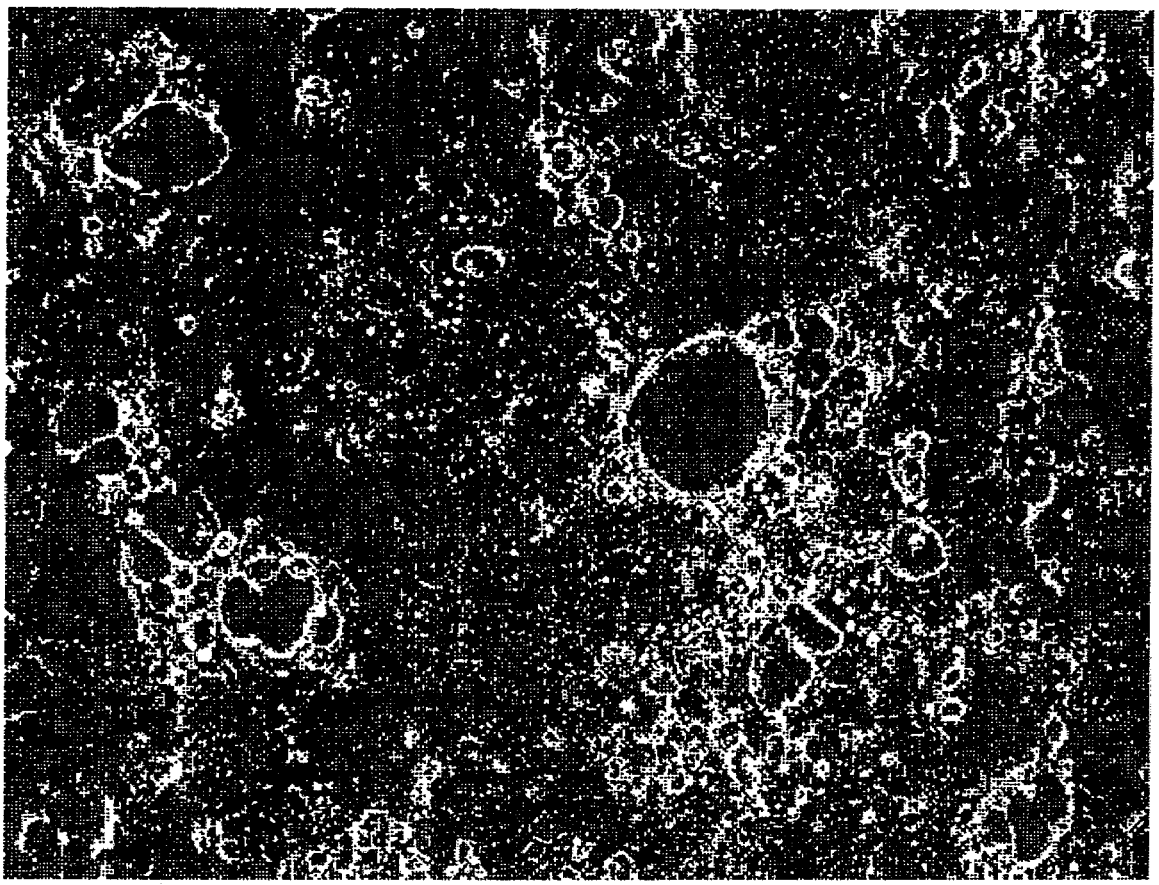
FIG. 43 shows conditions of the culture of Example 3, Sample No. 22 after 7 days.
Figure 44:
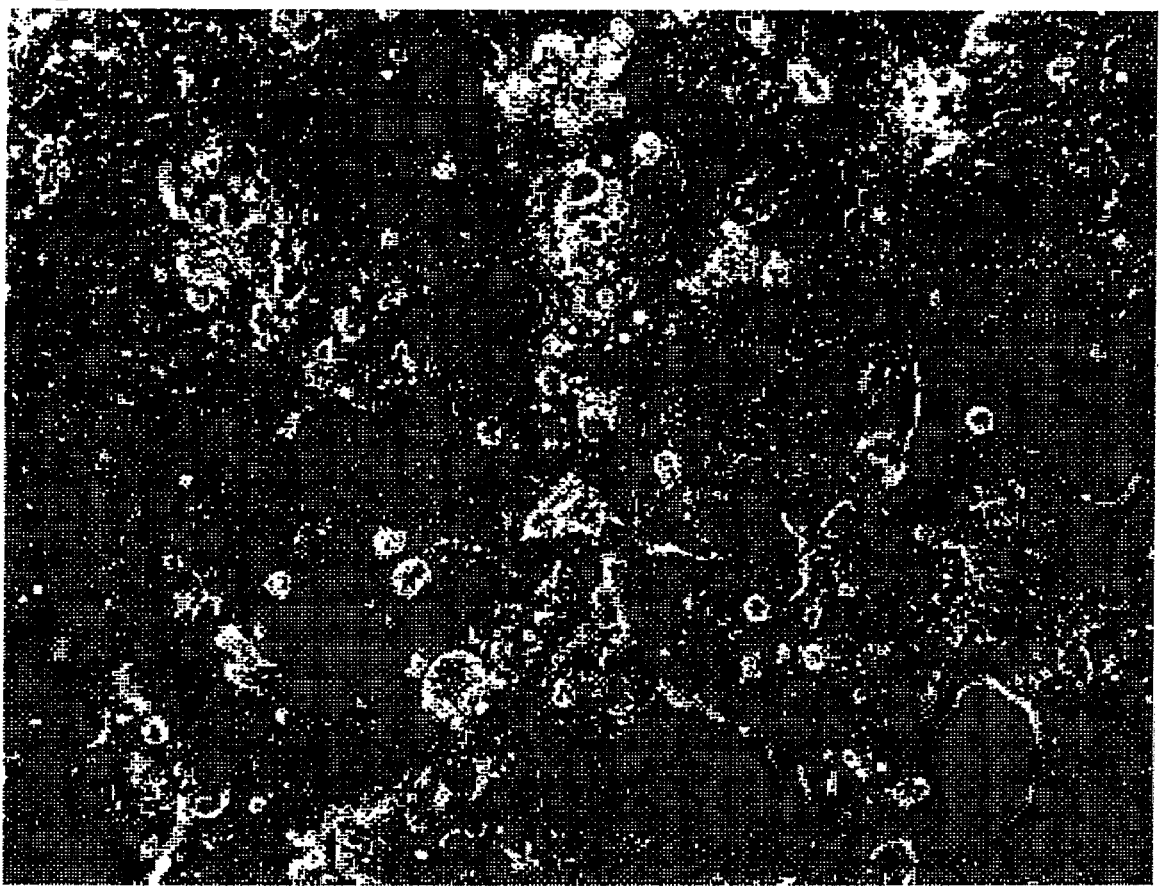
FIG. 44 shows conditions of the culture of Example 3, Sample No. 23 after 7 days.
Figure 45:
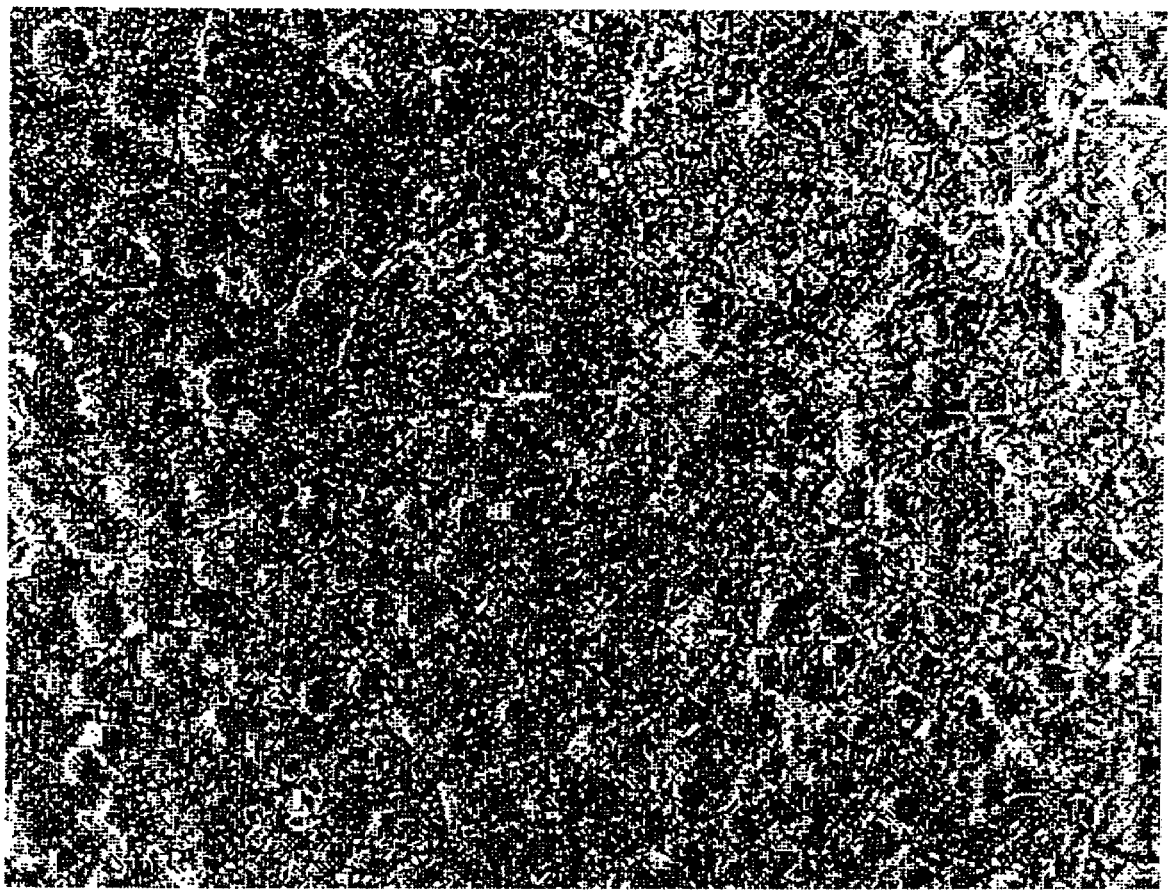
FIG. 45 shows conditions of the culture of Example 3, Sample No. 24 after 7 days.
Figure 46:
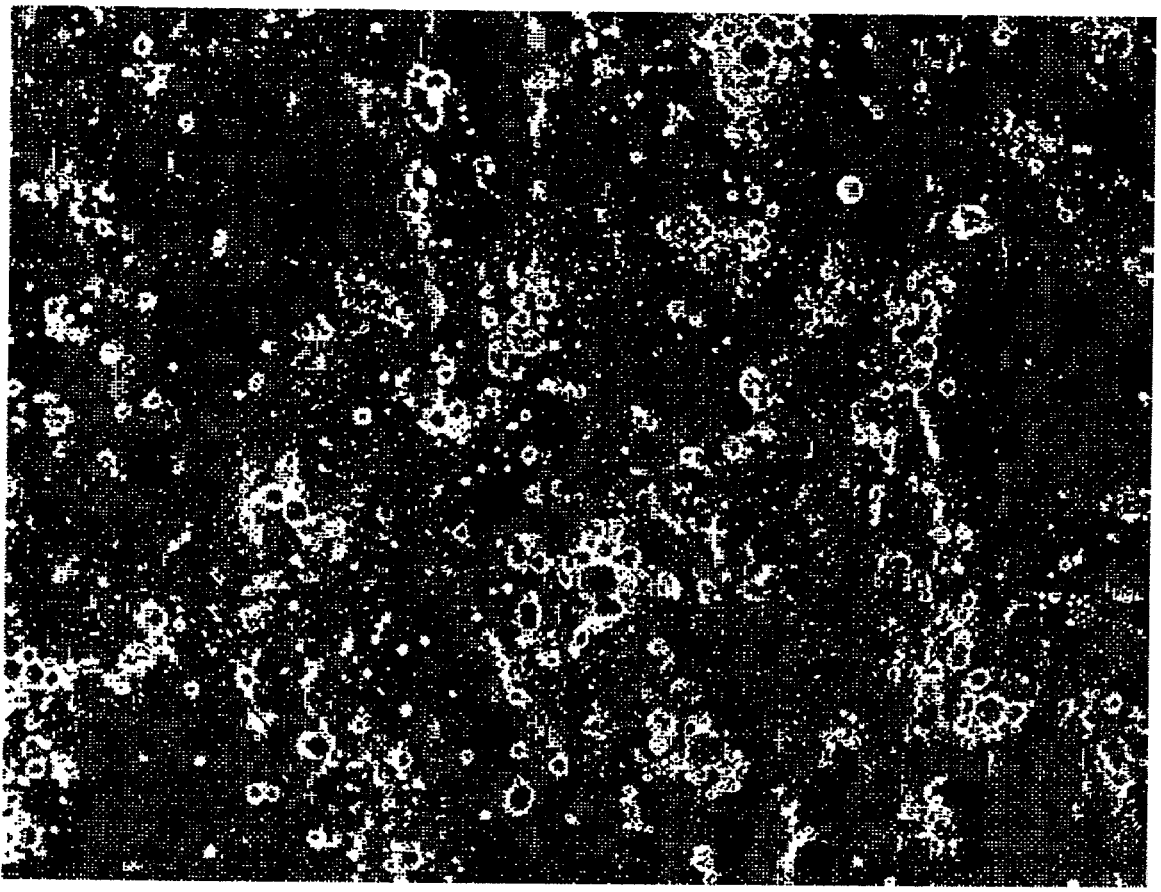
FIG. 46 shows conditions of the culture of Example 3, Sample No. 25 after 7 days.
Figure 47:
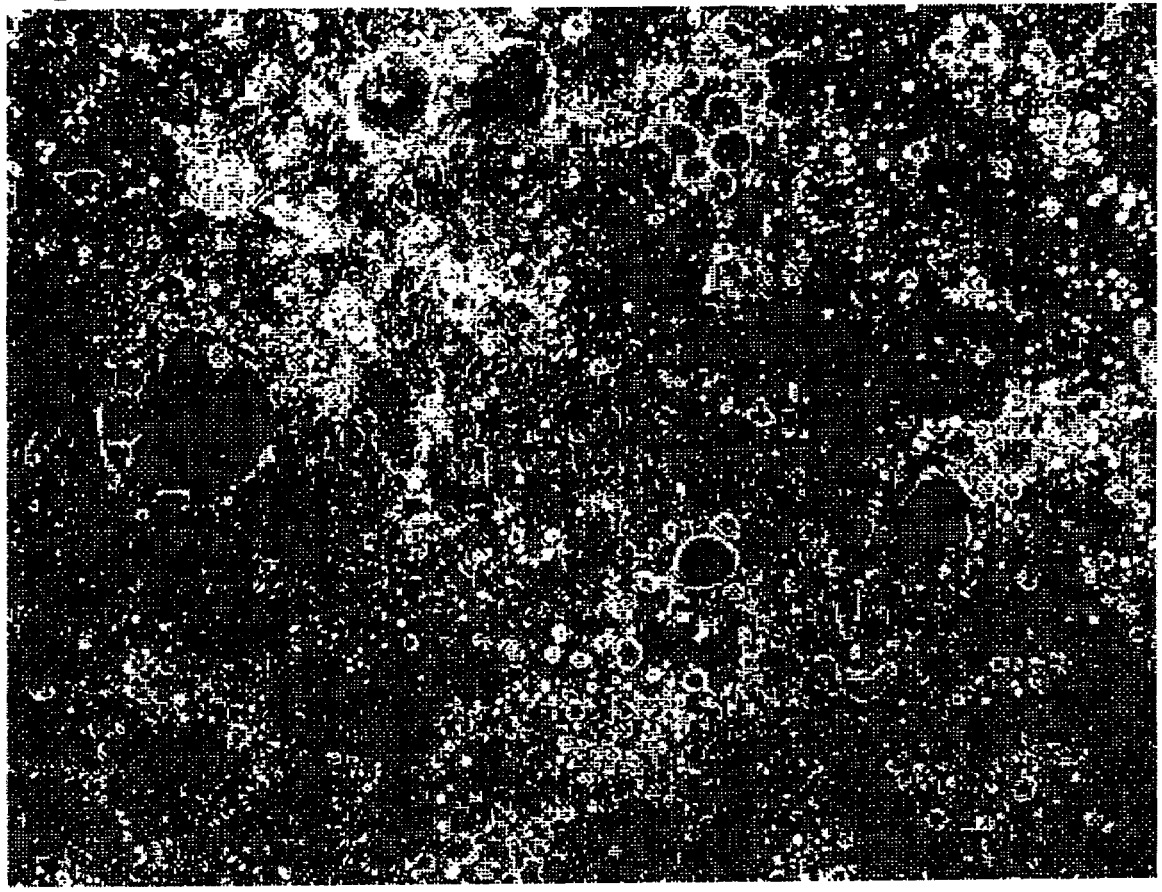
FIG. 47 shows conditions of the culture of Example 3, Sample No. 21 after 10 days.
Figure 48:
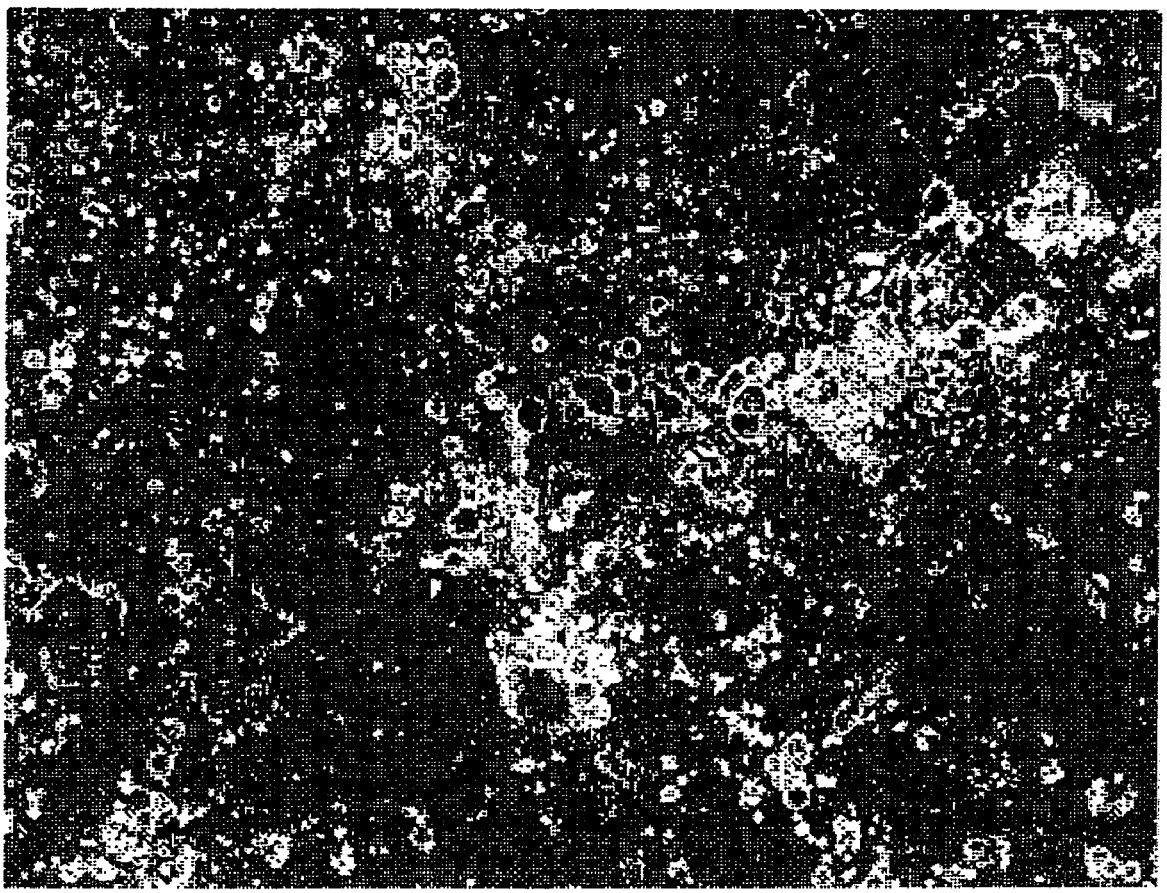
FIG. 48 shows conditions of the culture of Example 3, Sample No. 22 after 10 days.
Figure 49:
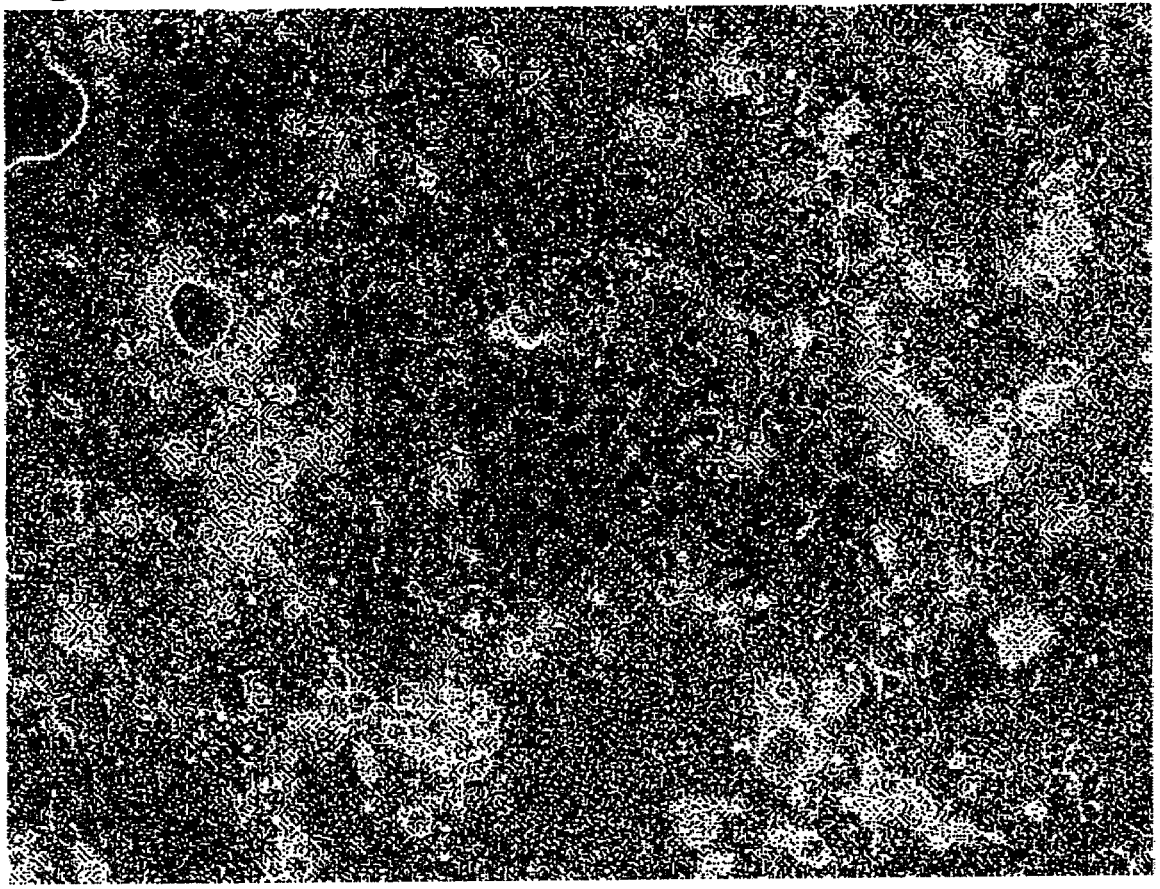
FIG. 49 shows conditions of the culture of Example 3, Sample No. 23 after 10 days.
Figure 50:
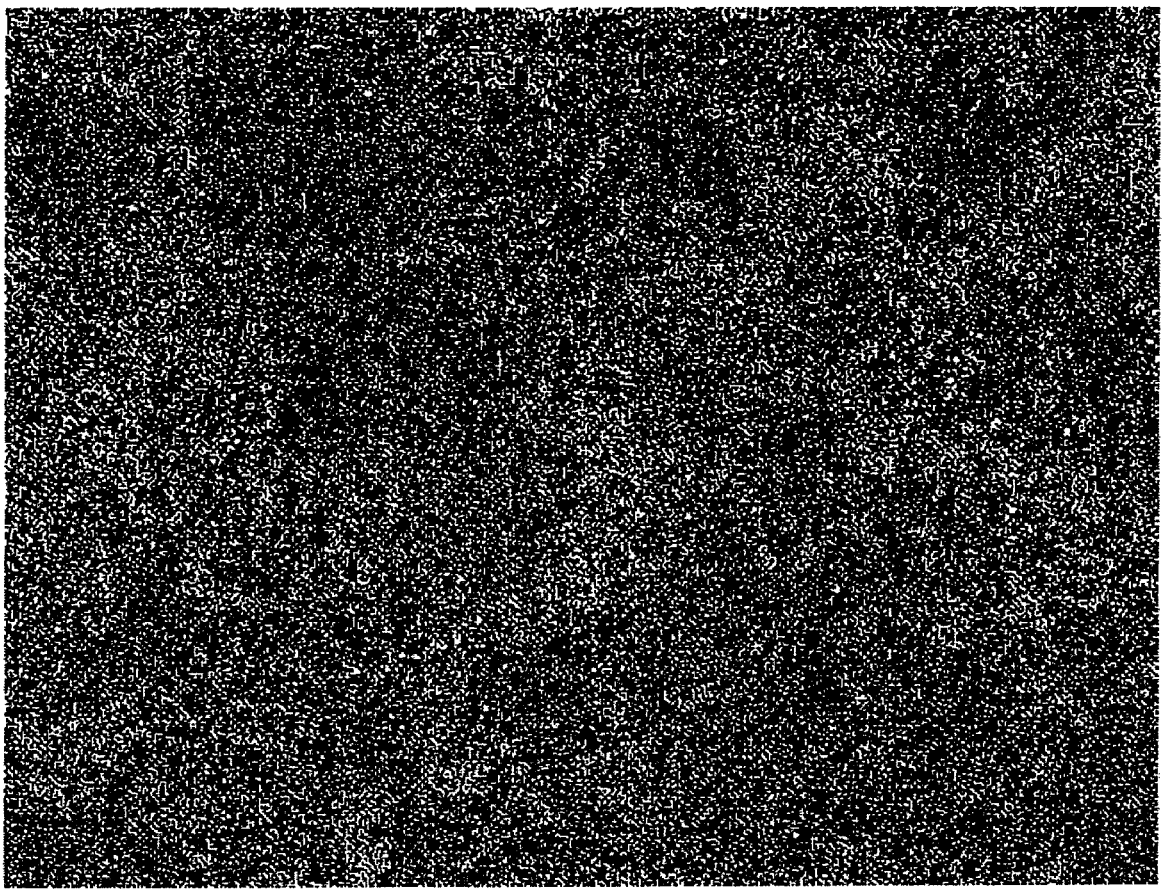
FIG. 50 shows conditions of the culture of Example 3, Sample No. 25 after 10 days.

In the assay of EROD shown in FIG. 16, Sample No. 2 exhibited the activity which is about the half, and Sample No. 3 exhibited the activity which is about ¼ of the collagen sample (Sample No. 5) under induced conditions (+3MC).

Example 3

HepG2 Cell

By repeating the procedure of Example 1, Sample No. 11 was prepared by using polyallyamine at a concentration of 0.1%, Sample No. 12 was prepared by using polyallyamine at a concentration of 0.01%, Sample No. 13 was prepared by using polyallyamine at a concentration of 1%, and Comparative Sample No. 14 was prepared by coating collagen.

HepG2 cells were cultivated by using these Sample Nos. 11 to 15.

The cell inoculated was well differentiated cell line HepG2 derived from human liver cancer purchased from Japanese Cancer Research, and this cell was inoculated at a density of $4\times10^4$ cells/cm$^2$ to a culture medium prepared by supplementing the culture medium of Example 1 excluding the auxiliary components with fetal bovine serum (FBS) to a final concentration 10% by volume.

FIGS. 17 to 21 show the condition of Sample Nos. 11 to 15 after 1 day; and FIGS. 22 to 26 show the condition of Sample Nos. 11 to 15 after 7 days.

With regard to the cell adhesion at the time of inoculation, the cell adhesion of Sample Nos. 11 to 14 was substantially the same as that of Comparative Sample No. 15. However, Sample No. 14 experienced cell death with morphological change after the inoculation. As demonstrated in the results of 1 day and 7 days after the inoculation in FIGS. 17 to 27, the samples which exhibited propagation equivalent to that of the Comparative Sample No. 15 were Sample Nos. 11 to 13.

Example 4

Caco-2 Cell

By repeating the procedure of Example 1, Sample No. 21 was prepared by using polyallylamine at a concentration of 0.1%; Sample No. 22 was prepared by using polyallylamine at a concentration of 0.01%; Sample No. 23 was prepared by using polyallylamine at a concentration of 0.001%; Sample No. 24 was prepared by using polyallylamine at a concentration of 1%, and Comparative Sample No. 25 was prepared by coating collagen.

Caco-2 cell was cultivated by using these Sample Nos. 21 to 25.

The cell inoculated was Caco-2 derived from human colorectal cancer which differentiates like small intestinal epithelium, and this cell was purchased from American Type Culture Collection (ATCC). The cell was inoculated at a density of $4\times10^4$ cells/cm$^2$ to a culture medium prepared by supplementing the culture medium of Example 1 excluding the auxiliary components with fetal bovine serum (FBS) to a final concentration 10% by volume.

FIGS. 27 to 31 show the condition of Sample Nos. 21 to 25 after 1 day; FIGS. 32 to 36 show the condition of Sample Nos. 21 to 25 after 3 days; FIGS. 37 to 41 show the condition of Sample Nos. 21 to 25 after 5 days; FIGS. 42 to 46 show the condition of Sample Nos. 21 to 25 after 7 days; FIGS. 47 to 50 show the condition of Sample Nos. 21 to 23, and 25 after 10 days.

With regard to FIGS. 27 to 31 showing the culture after 1 day, abnormality was clearly found in Sample No. 24, and abnormal cell adhesion could be confirmed in Sample No. 21. With regard to FIGS. 32 to 36 showing the culture after 3 days, abnormality was found in Sample Nos. 24 and 21 while good propagation was observed in Sample Nos. 22 and 23. With regard to FIGS. 37 to 41 showing the culture after 5 days, slight propagation was observed in Sample No. 21, and Sample No. 23 exhibited excellent results. With regard to FIGS. 42 to 46 and FIGS. 47 to 50 showing the culture after 7 days and after 10 days, Sample Nos. 22 and 23 exhibited good propagation.

As described above, the results of Sample Nos. 21 and 22 after cultivating for 7 days were equivalent to those of Comparative Sample No. 25. The results were most favorable in Sample No. 22.

Next, amount (g) of the glucose remaining in the culture medium after cultivating for 11 days was measured for the same samples. The results are shown in Table 1. In Table 1, Nos. 1 to 5 corresponds to Nos. 21 to 25, respectively.

TABLE 1

| Days after inoculation | No. 1 | No. 2 | No. 3 | No. 4 | No. 5 |
| --- | --- | --- | --- | --- | --- |
| 3@am | 1.13 g | 0.93 g | 0.451 g | 0.381 g | 0.001 g |
| 5@am | 0.965 g | 1.3 g | 0.291 g | 0.158 g | 0.008 g |
| 7@am | 1.04 g | 1.03 g | 0 g | 0.005 g | 0.002 g |
| 10@pm | — | — | 0.002 g | 0 g | 0 g |
| 11@pm | — | — | 0.007 g | 0.004 g | — |

*)"@am" means that the measurement was carried out in the morning, and "@pm" means that the measurement was carried out in the afternoon.

As demonstrated in Table 1, glucose had been consumed in Sample Nos. 22 and 23 to the level equivalent to that of Comparative Sample No. 25.

Figure 51:
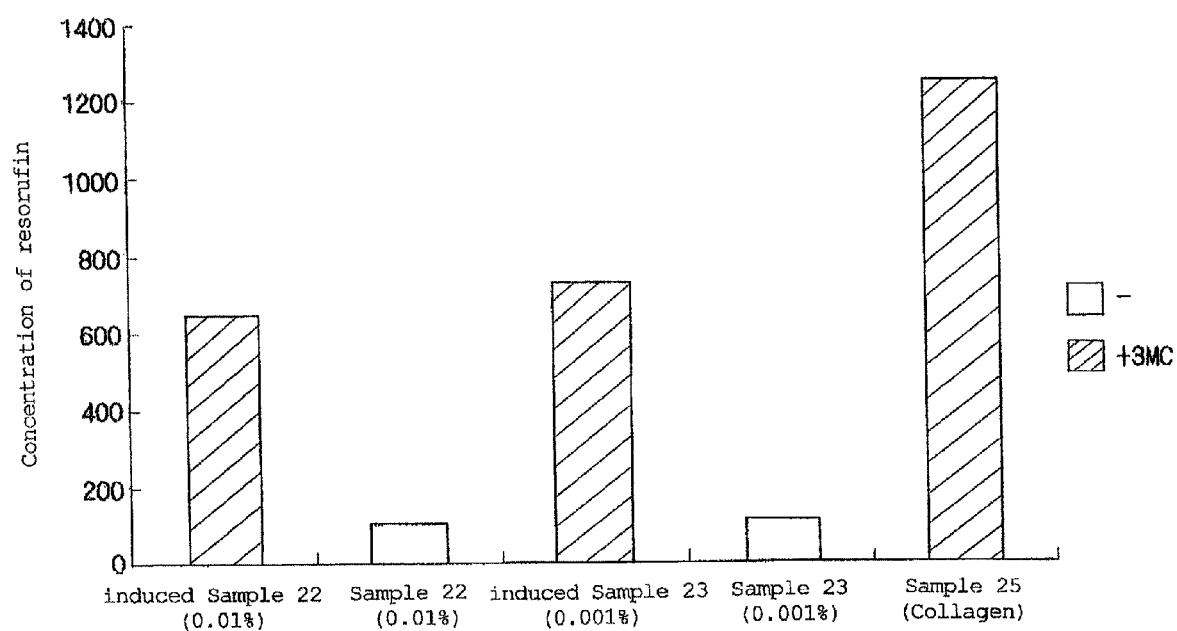
FIG. 51 is a graph showing the result of the resorufin evaluation for Example 3, Sample Nos. 23 to 25.

Sample Nos. 22 and 23 and Comparative Sample No. 25 were also evaluated for phase I activity of metabolizing enzyme cytochrome-P450 (CYP) by repeating the procedure of Example 2. The results are shown in FIG. 51. As demonstrated in FIG. 51, Sample Nos. 22 and 23 had an activity half that of the Comparative Sample No. 25 under induced conditions.

Example 5

The procedure of Example 1 was repeated except that the surface modification layer was directly formed without forming the underlying layer of the dichloro[2.2]paracyclophane to prepare Substrate Sample Nos. 31 to 34. The cultivation test was conducted as in the case of Example 1 by using these samples, and the test results were similar to those of Example 1. However, in the course of preparing a plurality of samples, the polymer layer was peeled in some samples presumably because of the mechanical stress applied in the step of washing and the like.

BENEFITS OF THE INVENTION

The present invention is capable of forming a surface modification layer by vapor deposition, and this enables commercially acceptable mass scale production of the cell culture substrate at a reduced cost. The layer formed by the surface modification is strong and durable, and therefore, the cell culture substrate has a high handling convenience. In addition, the surface modification layer can be deposited on the substrate having various shapes including those having a three dimensional structure, and the substrate may also comprise various types of material. Accordingly, the present invention has a wide range of applications.

When chloro-substituted [2.2]paracyclophane prepared by introducing chlorine in the 2.2]paracyclophane is deposited on the substrate by vapor deposition before the chemical vapor deposition of the formyl[2.2]paracyclophane, adhesion of the poly(formyl-p-xylylene) layer to the substrate is improved to reliably prevent peeling of the layer from the substrate. The thickness of the poly(formyl xylylene) layer can then be reduced, and this is economically advantageous.

The invention claimed is:
1. A method for the propagation or cultivation of cells comprising:
preparing a cell culture substrate, wherein said cell culture substrate
consists of a substrate and a surface modification layer, said layer consisting of a polymer comprising an amino group, wherein said polymer comprising said amino group is produced by reacting a polymer represented by the following formula (II):

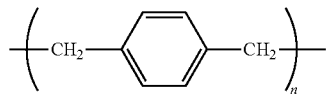
(II)

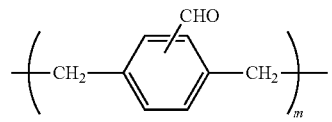

with a polymer having at least one amino group, —NH$_2$, capable of forming a Schiff base in a monomer of formula II, thereby forming a polymer layer constituting the layer formed by surface modification, wherein n is 0 or a positive integer, and m is a positive integer, the n and m representing degree of polymerization, wherein the surface modification layer improves affinity and adhesiveness of a cell, and wherein said formula (II) is formed by chemical vapor deposition of formyl[2.2]paracyclophane represented by the following formula (I):

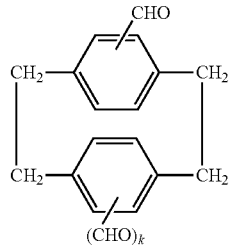
(I)

wherein k is 0 or 1;

providing cells in a medium;

inoculating the cells in said medium onto the cell culture substrate; and culturing the inoculated cells, wherein the cells adhere to the cell culture substrate.

2. The method for the propagation or cultivation of cells according to claim 1, wherein the polymer containing the amino group produced by the reaction constituting the layer formed by surface modification is represented by the following formula (III):

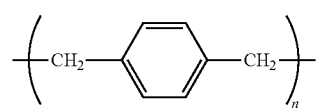
(III)

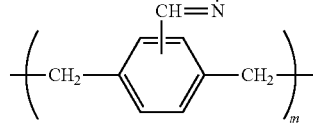

wherein n is 0 or a positive integer, m is a positive integer, X represents a group having a primary amine wherein the amino group is bonded directly to the carbon atom in the polymer backbone or via an intervening alkylene group containing 1 to 4 carbon atoms to carbon or nitrogen in the polymer backbone.

3. The method for the propagation or cultivation of cells according to claim 2, wherein the polymer backbone in X in the formula (III) is polyethylene, polyethyleneimine, or polymethylene amide.

4. The method for the propagation or cultivation of cells according to claim 2 wherein, in the formula (III), X is bonded to —CH$_2$ via carbon or nitrogen.

5. The method for the propagation or cultivation of cells according to claim 1, wherein the polymer having the amino group produced by the reaction constituting the surface modified layer is represented by the following formula (IV):

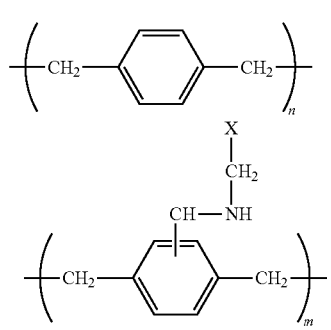
(IV)

wherein n is 0 or a positive integer, m is a positive integer, X represents a group having a primary amine wherein the amino group is bonded directly to the carbon atom in the polymer backbone or via an intervening alkylene group containing 1 to 4 carbon atoms to carbon or nitrogen in the polymer backbone.

6. The method for the propagation or cultivation of cells according to claim 5, wherein the polymer backbone in X in the formula (IV) is polyethylene, polyethyleneimine, or polymethylene amide.

7. The method for the propagation or cultivation of cells according to claim 5 wherein, in the formula (IV), X is bonded to —CH$_2$ via carbon or nitrogen.

8. The method for the propagation or cultivation of cells according to claim 1, wherein the polymer represented by the formula (II) is formed by chemical vapor deposition of formyl [2.2]paracyclophane represented by the formula (I) on an underlying layer of chloro-substituted [2.2]paracyclophane.

9. The method for the propagation or cultivation of cells according to claim 1, wherein the substrate is a three dimensional structure.

10. The method for the propagation or cultivation of cells according to claim 1, wherein the cells are animal cells.

11. The method for the propagation or cultivation of cells according claim 1, wherein the cells are embryonic stem cells.

12. The method for the propagation or cultivation of cells according to claim 1, wherein the resultant cultured cells are a primary cell culture.

13. The method for the propagation or cultivation of cells according claim 1, wherein said polymer having at least one amino group, —$NH_2$, is selected from the group consisting of:

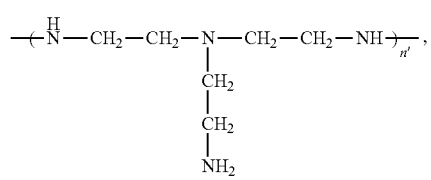
(1)

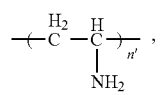
(2)

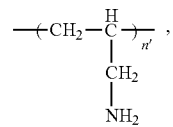
(3)

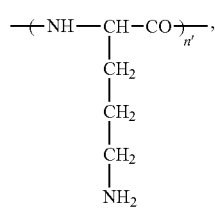
(4)

-continued

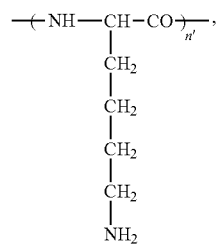
(5)

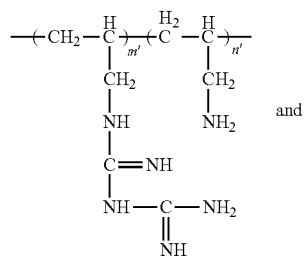
and

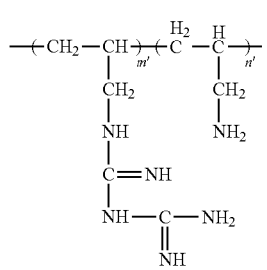
(PAC)

wherein n' and m' represent a degree of polymerization.

* * * * *